(12) United States Patent
Ninomiya et al.

(10) Patent No.: US 8,333,698 B2
(45) Date of Patent: Dec. 18, 2012

(54) ULTRASONOGRAPH

(75) Inventors: Atsushi Ninomiya, Ome (JP); Yoshimi Kasai, Nagareyama (JP); Masaru Inoue, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 258 days.

(21) Appl. No.: 12/635,227

(22) Filed: Dec. 10, 2009

(65) Prior Publication Data

US 2010/0094130 A1   Apr. 15, 2010

Related U.S. Application Data

(63) Continuation of application No. 12/516,384, filed on Feb. 12, 2010.

(30) Foreign Application Priority Data

Nov. 27, 2006   (JP) .................................. 2006-317956

(51) Int. Cl.
*A61B 8/00* (2006.01)
(52) U.S. Cl. ........................................ 600/437; 600/407
(58) Field of Classification Search .................. 600/437, 600/407
See application file for complete search history.

(56) References Cited

U.S. PATENT DOCUMENTS

| 4,625,731 | A | * | 12/1986 | Quedens et al. | 600/443 |
| 5,924,988 | A | | 7/1999 | Burris | |
| 2003/0236463 | A1 | * | 12/2003 | Mesaros et al. | 600/459 |
| 2006/0036177 | A1 | * | 2/2006 | Onodera | 600/459 |

FOREIGN PATENT DOCUMENTS

| JP | 06-090951 | 4/1994 |
| JP | 2004-053588 | 2/2004 |
| JP | 2005-526567 | 9/2005 |
| WO | WO 03/099129 | 12/2003 |

* cited by examiner

*Primary Examiner* — Tse Chen
*Assistant Examiner* — Joel F Brutus
(74) *Attorney, Agent, or Firm* — Antonelli, Terry, Stout & Kraus, LLP.

(57) ABSTRACT

An ultrasonograph includes a main body to which an ultrasonic probe is connected, an operation device having an operation switch, and a movable arm connecting the main body housing and the operation device. A bumper section is formed around the operation device, and wherein at least one probe container in which the ultrasonic probe is containable is formed at the bumper section.

9 Claims, 17 Drawing Sheets

(a)

(b)

(c)

(a)

(b)

(a)

(b)

ULTRASONOGRAPH

CROSS REFERENCE TO RELATED APPLICATION

This application is a continuation of U.S. application Ser. No. 12/516,384, filed Feb. 12, 2010, the contents of which are incorporated herein by reference.

TECHNICAL FIELD

The present invention relates to an ultrasonograph; and in particular to an ultrasonograph that can cope with various operation environments such as a standing posture, a sitting posture, and a posture for showing a monitor screen to an examinee.

BACKGROUND ART

A conventional ultrasonograph: contains an ultrasonic wave transceiver circuit, a digital scan converter (hereunder referred to as a DSC), and others in a housing equipped with a moving means as disclosed in, for example, Patent Documents 1 and 2; and further has a monitor to display images and an operation panel on the upper face of the housing. Such a conventional ultrasonograph makes it possible to: easily move the apparatus itself to the vicinity of an examinee lying on a bed; and diagnose the examinee with a probe since the whole apparatus is compactly arranged.

Some of conventional operation panels are accommodated to the operation of a standing or sitting posture by being equipped with an elevator mechanism, a slide mechanism in the horizontal direction, and moreover a swing mechanism in the horizontal direction. Further, some of conventional monitors make it possible for an operator to take operation postures and for an examinee to confirm an image by having a rotatable and tiltable structure.

[Patent Publication 1] JP-A No. 90951/1994
[Patent Publication 2] U.S. Pat. No. 5,924,988

DISCLOSURE OF THE INVENTION

Problems to be Solved by the Invention

Such a conventional ultrasonograph as stared above is devised so that the housing may not hit and interfere with a knee of an operator when the operator is in a sitting posture by installing an operation panel vertically movable with an elevator mechanism in the manner of largely hanging over toward the front of the housing. In such an ultrasonograph, however, only the operation panel is raised and lowered while the monitor remains on the upper face of the housing and hence the angle of the monitor has to be changed in conformity with the change of the operations between a standing posture and a sitting posture. Moreover, even though the angle of the monitor is changed, the line of sight of the operator to see the monitor is also changed and the resultant problem is that the operator is forced to operate with an uncomfortable posture.

Further, in such a conventional ultrasonograph, since the operation panel hangs over toward the front of the housing, the installation area increases in proportion to the extent of the overhanging. A further problem is that the possibility increases that the operation panel hits an obstacle while the ultrasonograph having the overhanging operation panel moves. For these reasons, it is necessary to take measures for protecting the operation panel.

Furthermore, since the housing of such a conventional ultrasonograph has basically the shape of a box, a connector device to which a probe is connected and the like are vertically or horizontally arranged on the vertical plane formed in front of the housing. The resultant problem is that the operations are hardly carried out since the connector device and the like are arranged at a position far back in the low and rear direction from the operation panel hanging over toward the front.

Further, since the housing of such a conventional ultrasonograph has basically the shape of a box, if the apparatus is used while the hosing comes close to an examinee lying on a bed, the vertically standing housing face shields the visual field of the examinee and the resultant problem is that the examinee feels enclosedness.

In addition, the operation panel of such a conventional ultrasonograph has a trackball as a coordinate indicator. It can be said that such a trackball is a coordinate indicator most suitable for such a compactly built ultrasonograph since a wide operating area is not required unlike a mouse. In a conventional ultrasonograph having a horizontally swingable operation panel, however, the trackball is installed at a position apart from the center of rotation of the operation panel and the resultant problem is that the position of the trackball moves largely in response to the rotation of the operation panel and thus the operation is hardly carried out.

In view of the above situation, an object of the present invention is to provide an ultrasonograph excellent in operability and mobility by: compactly containing an operation device having a group of switches on the upper face of the main body housing in the operation of a standing posture or a moving operation; and positioning the operation device in front in the operation of a sitting posture.

Means of Solving the Problems

In order to attain the above object: an ultrasonograph according to the present invention includes a main body housing, an operation device having operation switches, and a movable arm to connect the main body housing to the operation device; the operation device has a first housing having the operation switches, a second housing having an operation screen and a monitor screen to display a scanner image, and a connector to connect the second housing to the first housing; the main body housing has an inclined plane inclining rearward from a front face to an upper face; and the movable arm has an elevating function mechanical section to move the operation device along the inclined plane.

Further, the movable arm movably supports the operation device through an elevating function mechanical section to move the operation device by using an upper position on the inclined plane as a moving path so as to, in the state of maintaining the posture of the operation device, take a second posture wherein at least a part thereof hangs over the main body housing at a lower position on the inclined plane from a first posture wherein the operation device is contained within a projected area of the main body housing at an upper position on the inclined plane.

Effects of the Invention

According to the present invention, an operation device is located at a higher position above a main body housing in a first posture wherein the operation device having operation switches is located at an upper position on an inclined plane and at least a part of the operation device can be located in a manner of hanging over the main body housing at a lower position in front of the main body housing in a second posture wherein the operation device is located at a lower position of the inclined plane, and hence the operation device is compactly contained on the upper face of the main body housing during operations in a standing posture or moving and the operation device is located forward during operations in a sitting posture and thus it is possible to improve operability and mobility.

BEST MODE FOR CARRYING OUT THE INVENTION

An ultrasonograph according to the present invention is hereunder explained in detail in reference to FIGS. 1 to 17. FIGS. 1 to 16 represent the first embodiment and FIG. 17 represents the second embodiment. Here, identical parts and directions are shown with identical symbols and the duplication of explanation is avoided.

First Embodiment

An ultrasonograph according to the first embodiment is explained concretely in reference to FIGS. 1 to 16.

Firstly, the general structure of an ultrasonograph according to the present embodiment is explained in reference to FIG. 1. FIG. 1 is a perspective view showing the general structure of an ultrasonograph.

An ultrasonograph generally shown with the symbol 1 in FIG. 1 contains a main body housing 100 having universal wheels 101, an operation device 200, a movable arm 300 to movably connect the operation device 200 to the main body housing 100, and a plurality of ultrasonic probes 58.

The main body housing 100 has the universal wheels 101 at the four corners on the bottom face of the box-shaped housing and a housing handle section 102 to move the main body housing 100 is installed at the rear on the upper face. Then an inclined plane inclining upward toward the back from the front face to the upper face of the main body housing 100 is formed in the manner of forming a large arc shape and the inclined plane is used as a device allocation plane 103 in which various kinds of devices are stored. In the present embodiment, therefore, it is possible to: store devices, such as a controller, a digital scan converter (hereunder referred to as a DSC), and an electric power source, which are less frequently used by an operator, in the main body housing 100; and move the main body housing 100 containing connector devices 51 of the ultrasonic probes 58 and others in the device allocation plane 103 through the handle 102 and the universal wheels 101.

Further, the housing handle section 102 of the present embodiment is structured so as to support a bar-shaped grip 104 with the supports 105 on both the sides. Then a device allocation section 106 is installed between the bar-shaped grip 104 and the paired supports 105. The device allocation section 106 has a foldable table 107 and the appearance conforms to the shape of the inclined plane on the upper face of the main body housing 100 in the state where the table 107 is folded toward the main body housing 100 and various kinds of devices can be allocated on a table face 108 of the table 107 in a layered manner in the state where the table face 108 is horizontally placed.

Furthermore, the operation device 200 contains: a first housing 201 having operation switches 400 to operate the ultrasonograph 1; a second housing 202 having a monitor screen 203 to display an operation screen and a scanner image; an operation connector 204 to connect the second housing 202 to the first housing 201 at a prescribed angle; a bumper section 205 attached to the periphery of the first housing 201; and a keyboard 210 extractably stored at the lower part of the first housing 201.

In the present embodiment, each of the first and second housings 201 and 202 has the shape of a thin box and the second housing 202 is connected to the first housing 201 in a foldable manner through the operation connector 204. Then the operation switches 400 and the monitor screen 203 are allocated respectively on a first housing face 206 and a second housing face 207, those faces being hidden by each other in the state of folding the second housing 202 toward the first housing 201 in the direction indicated with the arrow Z3. Further, the operation connector 204 of the present embodiment connects the second housing 202 to the first housing 201 rotatably in the direction of the arrow Z4 around the center axis P4.

The first housing face 206 includes a trackball 401 installed nearly in the center of the first housing face 206 and a plurality of switches installed around the trackball 401. In the first housing face 206 of the present embodiment, the plurality of switches are aligned concentrically around the trackball 401 so that a planar plane constituting a palm rest 208 may be formed on the opposite side of the trackball 401 from the operation connector 204. Consequently, an operator can operate the most frequently used trackball 401 and the plurality of switches installed around the trackball 401 while wrists are supported by the palm rest 208.

The bumper section 205 is formed so as to: extend forward from the rear on both the sides of the first housing 201; and have an arched grip 209 at the front of the first housing 201. The arched grip 209 has the function of a handle to move and rotate the operation device 200 attached to the movable arm 300.

Further, in the present embodiment, at least the arched grip 209 of the bumper section 205 is located at a position lower than the first housing face 206 of the first housing 201. By so doing, it is possible to: locate the arched grip 209 at a lower position; and hence improve the operability when the operation device 200 is moved in a sitting posture.

Furthermore, by locating the arched grip 209 at a lower position, a space can be formed between the second housing 202 and the arched grip 209 even in the state where the second housing 202 is folded and hence the space an be used as a space for storing, for example, the ultrasonic probes 58 and a jelly container.

In addition, in the present embodiment, the arched grip 209 is located at a position on the same level as or a level lower than the bottom face of the first housing 201. By so doing, the arched grip 209 can have the retaining function when the keyboard 210 retracted under the bottom face of the first housing 201 is extracted in the direction of the arrow Z7.

The movable arm 300 has the function of using the upper space of the device allocation plane 103 obliquely formed from the front face to the upper face of the main body housing 100 as the moving path of the operation device 200. That is, the movable arm 300 has an elevating function mechanical section 301 that makes it possible to take a first posture Q1 wherein the operation device 200 is located at an upper position of the inclined device allocation plane 103 and a second posture Q2 wherein the operation device 200 is located at a lower position of the device allocation plane 103.

The movable arm 300 of the present embodiment is: exposed at an end from an arm transfer groove 109 formed on one side of the inclined plane; and attached at the other end to a rotation axis P1 formed at a prescribed position in the arm transfer groove 109 so as to be rotatable around the rotation axis P1. In the movable arm 300, an attachment mechanical section 350 to attach the operation device 200 to the exposed end is installed. Consequently, by rotating the movable arm 300, it is possible for the operation device 200 attached to the attachment mechanical section 350 to take both the first posture Q1 and the second posture Q2. Here, the movable arm 300 includes a link mechanism and hence it is possible to keep the angle of the operation device 200 attached to the attachment mechanical section 350 constant even when the movable arm 300 is rotated.

Further, the attachment mechanical section 350 has: a horizontal movement mechanical section 360 to move the operation device 200 in the horizontal direction (the arrow Z5) perpendicular to the moving direction of the movable arm 300 (the arrow Z1); a tilt mechanical section 370 to adjust the angle of the first housing 201; and a rotation mechanical section 380 to revolve the operation device 200.

The horizontal movement mechanical section 360 moves the operation device 200 so that the operation device 200 may take the state where the operation device 200 is located above the device allocation plane 103 and the state where the operation device 200 deviates from the device allocation plane 103 by moving the operation device 200 in the horizontal direction (the arrow Z5). By so doing, it is possible to: move the operation device 200 in the transverse direction of the main body housing 100; and thus facilitate the operation posture of an operator and the information service to a patient.

Further, the tilt mechanical section 370 can swing the first housing 201 in the direction shown with the arrow Z6. By so doing, it is possible to: arbitrarily set the angle of the first housing face 206 having the operation switches 400; and hence adjust the angle of the first housing face 206 in conformity with the posture of an operator. Moreover, in the present embodiment, since the second housing 202 having the monitor screen 203 is fixed to the first housing 201 through the operation connector 204, it is also possible to automatically adjust the angle of the monitor screen 203 in accordance with the change of the angle of the first housing face 206.

Furthermore, the rotation mechanical section 380 can revolve the operation device 200 around the rotation axis P2 in the manner of shaking a head. By so doing, it is possible to rotate the first housing 201 itself having the operation switches 400 and hence it is possible to: adjust the key arrangement of the operation switches 400 in the direction conforming to the posture of a user; and also rotate the second housing 202 having the monitor screen 203 in accordance with the rotation.

Further, the rotation axis P2 is formed at a position where it passes through the rotation center of the trackball 401. Then the operation switches 400 are allocated around the trackball 401. Consequently, the arrangement of the operation switches 400 formed around the trackball 401 located on the rotation axis P2 is not changed even when the operation device 200 is rotated and hence the operation such as touch typing is facilitated.

In addition, in the present embodiment, a plurality of ultrasonic probes 58 can be set up. In order to realize the full readiness of the ultrasonic probes 400, a plurality of probe containers 110 to contain the ultrasonic probes 58 are formed at the bumper section 205 and on both the sides of the device allocation plane 103 and an end of each of the cords of the ultrasonic probes 58 is connected to each of the plurality of connector devices 51 allocated on the device allocation plane 103. In the present embodiment, it is possible to improve usability by containing a currently used ultrasonic probe 58 at the bumper section 205 and containing a spare ultrasonic probe 58 in a probe container 110 on the side of the main body housing 100. Further, each of the probe containers 110 on the side of the main body housing 100 also has the function of hooking each of the cords and hence it is possible to contain the plurality of cords in an arranged manner without confusion.

Then one of the main features of the present embodiment is that the first housing 201 having the operation switches 400 is movable and can take the first posture Q1 wherein the first housing 201 is located at an upper position within the projected area of the main body housing 100 and the second posture Q2 wherein a part of the first housing 201 hangs over the projected area of the main body housing 100 at a lower position.

In an existing technology of this kind, a table containing operation switches 400 hangs over a main body housing forward in order for an operator to be able to operate in a sitting posture and the operator can operate in a standing posture by moving the forward overhanging table upward. That is, in a conventional technology, since the structure is mainly based on a sitting operation, a problem here is that the overhanging table is an obstacle in a standing posture although good operability is obtained in a sitting posture. Moreover, the lower part of the table forms a dead space in the state where the table is lifted upward and another resultant problem is that the size of an ultrasonograph 1 increases in a standing posture. An additional problem is that the forward overhanging table is an obstacle when an ultrasonograph 1 is moved.

In the present embodiment in contrast, it is possible to solve the problems of the conventional technologies since the operation device 200 takes: a feature of forward overhanging suitable for a sitting posture in the second posture Q2 conforming to a sitting posture; and a feature suitable for a standing posture at a higher position within the projected area of the main body housing 100 in the first posture Q1 conforming to a standing posture.

Furthermore, another main feature of the present embodiment is that the second housing 202 having the monitor screen 203 to display the operation screen and a scanner image is movable and can take the first posture Q1 and the second posture Q2 while the relative relation to the first housing 201 having the operation switches 400 is maintained.

In an existing technology of this kind, a table having operation switches 400 and a monitor are structurally separated from each other. That is, in a conventional technology, a monitor screen 203 to display an operation screen and a scanner image is installed at an upper portion of a main body housing 100 and only the table has an elevating mechanism. In a conventional technology, an auxiliary display related to operation switches 400 for operation confirmation and operation display is installed on the table in some cases, but a monitor screen 203 to display an operation screen and a scanner image is installed in the main body housing 100 as stated above. Consequently, vertical movement of the table is not linked to the height of the monitor screen 203 and a resultant problem is that the line of the sight of an operator for monitoring and the posture of the operation switches 400 are different between sitting operation and standing operation.

Further, the operation switches 400 and the monitor screen 203 are individually installed separately from each other and a resultant problem is that mechanical sections for vertical movement, rotation, and tilting have to be installed independently. In the present embodiment, the problem can be solved.

Furthermore, another main feature of the present embodiment is that an inclined plane largely inclining upward toward the back from the front face to the upper face of the main body housing 100 is formed and the inclined plane is used as the device allocation plane 103 to contain various devices.

In a conventional technology, similar kinds of connector devices are installed on the vertical face of the main body housing 100 in a layered manner and hence a resultant problem is that cord joints formed at the front faces of the connector devices overlap vertically and are hardly attachable and detachable. In this regard, by adopting an inclined device allocation plane, an upper device can be installed so as to be retracted backward (in the back) from a lower device in the various devices such as the vertically-layered connector devices 51 and hence the aforementioned conventional problems can be solved.

Further, another main feature of the present embodiment is that the inclined plane largely inclining upward toward the back is used as the transfer path of the first housing 201 or the operation device 204.

In a conventional technology, the table having the operation switches 400 is structured so as to move vertically and hence a resultant problem is that a dead space is formed at the lower part thereof in the state where the table is located at an upper position. Further in a conventional technology, the table is in the state of hanging over forward regardless of the vertical location and hence a resultant problem is that the overhanging table hinders except the case of sitting operation. In the present embodiment, the aforementioned problems of the conventional technologies can be solved.

Further, another main feature of the present embodiment is that the second housing 202 is made to be foldable toward the first housing 201. By so doing, it is possible to: adjust the angle of the operation device 200 having the monitor screen 203 to the first housing 201 having the operation switches 400; and hence improve the visibility during operation. Further, it is possible to: hide the monitor 203 and the operation switches 400 between the two housings by folding the second housing 202; and improve the roominess.

Furthermore, another main feature of the present embodiment is that the operation connector 204 to connect the second housing 202 to the first housing 201 has the function of horizontally rotating the second housing 202 in addition to the function of folding. By so doing, it is possible to improve not only the visibility of an operator but also the visibility of an examinee.

Further, another main feature of the present embodiment is that the movable arm 300 has a structural means for always maintaining the operation device 200 attached to the tip thereof in an identical posture regardless of the movement of the movable arm. In the present embodiment, the arm 300 includes a link mechanism and hence the first housing 201 attached to the movable arm 300 is always maintained in an identical posture.

In addition, another main feature of the present embodiment is that the attachment mechanical section 350 has a posture change mechanism to change the posture of the attachment mechanical section 350. In the present embodiment, it is possible to take various operation postures and provide information to an examinee by having a horizontal movement mechanical section 360 as a posture change means and thus increasing the motion distance of the operation device 200 in the transverse direction. Moreover, it is possible to: expose the device allocation plane 103 located under the transfer path of the operation device 200 in accordance with the movement of the operation device 200 in the transverse direction; and hence improve the operability of the various devices located on the device allocation plane 103.

In the present embodiment, it is possible to: arbitrarily set the angle of the first housing 201 having the operation switches 400 by installing the tilt mechanical section 370 as another posture change mechanism; and hence improve the operability of the operation switches 400.

Moreover in the present embodiment, an operator can face the operation device 200 in conformity with the position of the operator by installing the rotation mechanical section 380 as another posture change mechanism and hence it is possible to improve the operability of the operation switches 400.

Further, another main feature of the present embodiment is that the operation switches 400 are allocated so that the center of the trackball 401 may be located on the rotation axis P2 of the rotation mechanical section 280. By so doing, it is possible to keep the frequently used trackball 401 at the home position regardless of the rotation of the operation device 200, and hence an operator can easily recognize the location of all the switches and it is possible to improve the operability including touch typing operation. In the present embodiment in particular, by allocating keys and operation buttons configuring the operation switches 400 on concentric circles around the trackball 401, it is possible to further improve the operability.

Further, another main feature of the present embodiment is that: the bumper section 205 is installed around the first housing 201; and, in addition to the function of the bumper to protect the operation device 200, the function of a handle to move the operation device 200, the function of storing frequently used ultrasonic probes 58, other devices, and accessories, the function of supporting the keyboard 210 stored at the lower portion of the first housing 201, and other functions are granted to the bumper section 205.

Furthermore, another main feature of the present embodiment is that the probe containers 110 to retain less frequently used ultrasonic probes 58, cords, and others are disposed on both the sides of the device allocation plane 103. By so doing, it is possible to improve the usability of the ultrasonic probes 58 and the neatness of the cords.

The concrete structure of an ultrasonograph 1 according to the first embodiment having the aforementioned features is hereunder explained further in detail.

Firstly, the configuration of the ultrasonograph 1 is explained in reference to FIG. 2. FIG. 2 is a block diagram of the ultrasonograph 1. In FIG. 2, the ultrasonograph 1 includes: an ultrasonic probe 58 having a group of ultrasonic transducers; an ultrasonic transceiver circuit 52 to supply high-voltage pulses to the ultrasonic probe 58; a connector device 51 to connect the ultrasonic transceiver circuit 52 to the ultrasonic probe 58; a digital scan converter (hereunder referred to as a DSC) 55 to convert obtained echo signals into digital signals; a memory device 56 including an image memory, a graphic memory for common use, a graphic memory for an operator, and other memories; a monitor device 57 having the monitor screen 203; an input device 54 including the operation switches 400; a control device 53 to integrally control the ultrasonograph 1; an auxiliary device 59 such as an electrocardiogram measuring device connected if necessary; and an electric power supply device 60 to supply electric power to various devices.

The ultrasonic transceiver circuit 52: supplies high-voltage pulses for sending waves to the ultrasonic transducers in the ultrasonic probe 58; also amplifies, phase-conditions, and detects the echoes reflected from the inside of an examinee body and received with the probe; and inputs the output signals to the DSC 55. In the present embodiment, a plurality of the ultrasonic probes 58 can be attached. Each of the ultrasonic probes 58 has a cord of a prescribed length and is connected to a connector device 51 installed in accordance with each of the ultrasonic probes 58 through a cord joint 51a formed at the tip of the cord.

The DSC 55: converts the input echo signals into digital signals; writes ultrasonic beams one beam by one beam repeatedly in a memory every time when the beams are sent and received; and reads out the stored content in synchronization with the scanning of the monitor device 57. The graphic memory for common use constituting the memory device 56 is a graphic memory to display additional information displayed on the monitor device 57 through the DSA 56 in the manner of being superimposed on an ultrasonic image, for example, information that does not give the feelings of insecurity to an examinee, such as the scale of an ultrasonic image, a body mark showing the position of the examinee body where an ultrasonic probe 58 is placed, and distance measurement information. Further, the graphic memory for operation in the memory device 56 is a graphic memory that displays only the additional information needed for the diagnosis by an operator, for example, only literal information such as a disease name and ID information of an examinee and symbolic information such as an arrow indicating a legion, in the manner of superimposing on an ultrasonic image on the monitor device 57.

In the ultrasonograph 1, the detection is started by: operating the input device; setting up an ultrasonic scanning mode and the display of measurement additional information; and putting an ultrasonic probe 58 to the portion of an examinee to be examined. The ultrasonic waves sent from the ultrasonic probe 58 to the interior of an examinee body are reflected at the boundary of body organs having different acoustic impedances and received with the probe. The received echoes are: amplified, phase-conditioned, and detected with the ultrasonic transceiver circuit 11; input into the DSC 55 as the signal corresponding to one ultrasonic scanning line; subjected to D/A conversion; and written into a memory. The writing into the memory is carried out repeatedly every time when ultrasonic signals are sent and received in different directions.

The image data written in the memory are read out in synchronization with the display scanning of the monitor device 57, subjected to D/A conversion, and supplied to the monitor device 57 as luminance signals, and as a result an ultrasonic image is displayed on the screen. The control device 53 reads out data also from both the graphic memory for common use and the graphic memory for an operator in synchronization with the read-out of the image data from the DSC 55. In the present embodiment, the contents in the graphic memory for an operator may not be displayed when the monitor screen 203 of the monitor device 57 is shown to an examinee. The switching of the monitor screen 203 can be operated through the operation switches 400.

Successively, the configurations of the devices explained in FIG. 2 are explained concretely in reference to FIGS. 3 and 4. FIG. 3 shows conceptual views showing the configurations of the devices in the ultrasonograph 1; FIG. 3(a) represents a front view and FIG. 3(b) represents a left side view. FIG. 4 shows device allocation views of the device allocation plane; FIG. 4(a) is a schematic sectional view of the third device container, FIG. 4(b) a front view of the device allocation plane, FIG. 4(c) a schematic sectional view of the third device container according to another embodiment, and FIG. 4(d) a front view of the device allocation plane according to another embodiment.

In FIG. 3, in the present embodiment, the center of gravity of the ultrasonograph 1 is lowered and mobility and stability are improved by installing the electric power supply device 60 that is the heaviest device at the lowermost portion of the main body housing 100. A first device container 70 containing the ultrasonic transceiver device 52 and the DSC 55 is installed above the electric power supply device 60, a second device container 71 to contain the control device 53 and the memory device 56 is installed rearward above the first device container 70, and a third device container 72 to contain a plurality of connector devices 51 and an elevating function mechanism container 302 to contain the movable arm 300 are installed side by side in front of the second device container 71.

A space is secured in front of the first device container 70 as a storage rack 70a opening toward the front of the main body housing 100. In the present embodiment, it is possible to contain the auxiliary device 59 in the storage rack 70a. The main body housing 100 according to the present embodiment has an appearance configuration inclining from the front face toward the upper face so as to form a large arc as shown in the side view of FIG. 3(b). The storage rack 70a can be used as an ordinary rack by being installed along the vertical plane of the arc.

Further, the third device container 72 has a space about a quarter of a circle and is a space that can hardly contain devices. In the present embodiment, by containing the same kinds of plural connector devices 51 each of which has a thin-box-shaped housing in the third device container 72 and allocating a connector device 51 installed at an upper position to a position posterior to a connector device 51 installed at a lower position in a vertically layered manner, the dead space is reduced in the oddly-shaped third device container 72 and the operability of the connector devices 51 is improved. The specific configuration is explained further in reference to FIG. 4.

In FIGS. 4(a) and 4(b), in the present embodiment, each of the connector devices 51 is located so that the longitudinal direction of a connector device 51 may coincide with the direction of each of the radial lines S1 that pass through the center of the arc-shaped device allocation plane 103. In the configuration, a connector device 51c located at an upper position is located more backward than a connector device 51b located at the lowermost position and a connector device 51d located at a further upper position is located more backward than the connector device 51c. As a result, a cord joint 51a attached to the front face of a connector device 51 is located more backward as the connector device 51 is located at a higher position and hence the attachment and detachment of the cord joints 51a are facilitated. Moreover, the usability of the cord joints 51a also improves because the cords connected to the cord joints 51a also extend radially.

Further, the front face panels 51e of the connector devices 51 to which the cord joints 51a are attached are contained on the plane identical to the arc-shaped device allocation plane 103, thus the number of the cords joints 51a protruding from the front face panels 51e and the number of the cords are the same, and hence the transfer path of the operation device 200 formed at the upper portion of the device allocation plane 103 can be secured more easily. In addition, by adopting the radial allocation in the third device container 72, an appropriate volume of spaces can be formed around the connector devices 51 and hence the effect of heat dissipation is also expected.

Here, in the above embodiment, explanations are made with the case where radial device allocation is adopted for the third device container 72 but the present invention is not limited to the case. For example, another device allocation may be adopted as shown in FIGS. 4(c) and 4(d). That is, FIG. 4(c) shows the case where the connector devices 51 are vertically layered while the longitudinal directions of the connector devices 51 are directed in the horizontal direction. In the case too, by allocating an upper connector device 51c to a position more backward than a lower connector device 51b (in a deviated manner), it is possible to: allocate the plurality of connector devices 51 in the oddly-shaped third device container 72; and moreover obtain effects similar to the case shown in FIG. 4(*a*).

Further, FIG. 4(*d*) shows the case where the connector devices 51 of transverse postures are obliquely arranged along the arc plane (including an inclined plane) in a front view of the device allocation plane 103 while the arrangement shown in FIG. 4(*c*) is maintained. In the configuration, the connector devices 51 in an obliquely inclined transverse posture are layered vertically in an oblique posture so that the sides where cord joints 51*a* are connected (the left side in the figure) may be located more forward than the other sides (the right side in the figure). Moreover, the front face panels 51*e* are located on the plane identical to the arc-shaped plane (the inclined plane) of the device allocation plane 103 and hence the front face panels 51*e* to which the cord joints 51*a* are connected are contained in the posture inclining to the right. As a result, the cord joints 51*a* vertically connected to the front face panels 51*e* are located in the center and have an upward inclining posture and hence the attachment and detachment of the cord joints 51*a* are facilitated.

In FIG. 3 again, an open arm transfer groove 109 is formed at the upper portion of the elevating function mechanism container 302. An end of the movable arm 300 is rotatably fixed in the interior of the elevating function mechanism container 302 through the rotation axis P1. Consequently, by rotating the movable arm 300 around the rotation axis P1, it is possible to move the operation device 200 attached to the other end of the movable arm 300 between the first posture Q1 and the second posture Q2.

Further, in the present embodiment, it is possible to install a table face 108 that can be used as a fourth device container at an upper portion of the main body housing 100. The table face 108 can be formed with a foldable table 107 as explained in FIG. 1 or can be formed with a table stage 111 having a robust structure in place of the table 107 as shown in FIG. 3. The auxiliary device 59 may be installed on the table face 108 constituting the upper face of the table stage 111. In the present embodiment, the explanations are made on the basis of the case where a video device 81 to record motion pictures and a printer 82 are placed in a layered manner. The fourth device container is located at the uppermost position of the main body housing 100, hence is close to the line of sight of an operator in a standing posture, thus can be installed without the interference with other devices, and is excellent in operability and usability.

Furthermore, in the present embodiment, the attachment mechanical section 350 that can function as a fifth device container is installed at the tip portion of the movable arm 300. The operation device 200 on which the frequently used monitor screen 203 and operation switches 400 are collectively allocated can be attached to the attachment mechanical section 350. Moreover, the operation device 200 can be easily adjusted to the operation postures (the first posture Q1 and the second posture Q2) of an operator through the movable arm 300.

Successively, the appearance configuration of the ultrasonograph 1 is explained further in detail in reference to FIGS. 5 to 13. FIGS. 5 and 6 show external views of the ultrasonograph 1; FIG. 5(*a*) is a plan view, FIG. 5(*b*) a bottom view, FIG. 5(*c*) a front view, FIG. 5(*d*) a right side view, FIG. 6(*a*) a back view, FIG. 6(*b*) a left side view, and FIG. 6(*d*) is a left side view in the state where the movable arm is moved. Further, FIG. 7 is a perspective view showing the folding structure of the table. FIG. 8 is a plan view of the operation device. FIG. 9 is a right side view of the operation device in the state where the second housing is closed. FIG. 10 is a right side view of the operation device in the state where the second housing is opened. FIG. 11 is an exploded structural view of the operation connector. FIG. 12 shows external views in the state where the keyboard is extracted; FIG. 12(*a*) is a view in the state of usage and FIG. 12(*b*) is a schematic transverse sectional view. FIG. 13 shows detail views of the operation switches; FIG. 13(*a*) is a plan view of the operation device and FIG. 13(*b*) is a sectional view of a rotary switch.

In FIG. 5, the main body housing 100: has an anteroposteriorly-long rectangular bottom shape where the depth D1 is larger than the width W1; and is vertically long with the height H1 larger than the depth D1. Here, in the present embodiment, the width W1, the depth D1, and the height H1 are set at 450 mm, 746 mm, and 982 mm, respectively. As shown in FIG. 5(*b*), the front and back portions on the bottom face of the main body housing 100 are notched into concaves and the universal wheels 101 are attached to the concaves 225. By the allocation of the universal wheels 101, the rotation region of the universal wheels 101 is secured, the main body housing 100 appears to be compact when it is viewed from the anteroposterior directions, and the first device container 70 is secured between the anteroposterior universal wheels 101 as explained in FIG. 3.

Further, the front face of the main body housing 100 is formed in the shape of a large arc from the front face toward the upper face as shown in FIG. 5(*c*). That is, as shown in FIG. 5(*d*), the shape of the main body housing 100 in the side view includes a quarter of a circle (the upper left region of the regions equally divided by the horizontal line and the vertical line, both lines passing through the center axis of the circle).

At the lower portion on the front face corresponding to the lower portion of the arc shape, the storage rack 70*a* including a plurality of shelves is formed and the auxiliary device 59 can be stored. Above the storage rack 70*a*, the device allocation plane 103 having an arc shape gradually retracting toward the upper direction is formed, the arm transfer groove 109 is formed on one side thereof, and a plurality of device container openings 112 are formed vertically on the other side. By installing the connector devices 51 in the plurality of device container openings 112, the device allocation explained in FIG. 4 is realized.

Further, the vicinity of the upper portion of the device allocation plane 103 is a space where large devices such as the connector devices 51 are hardly contained. Consequently, in the present embodiment, the hardly containable space is used as the storage space for a jelly container 83. That is, as shown in FIG. 5(*d*), a container storage recess 113 in which a cylindrical jelly container 83 is stored in a transverse posture is formed in the vicinity of the upper portion of the device allocation plane 103 and the jelly container 83 can be stored in the container storage recess 113 so that about a half of the container may be embedded.

Furthermore, in the present embodiment, the main body housing 100 showing the shape of a quarter of a circle in a side view is adopted but the uppermost portion of the quarter circle shape is a space not suitable for containing a device. Consequently, in the present embodiment, the uppermost portion of the quarter circle shape is cut off along an inclined plane 114 inclining backward. Then the inclined plane 114 is used as the space for the installation of the table face 108 that can be used as the fourth device container. To the table face 108, the foldable table 107 can be attached as shown in FIG. 1 or a robust table stage 111 can be attached in place of the table 107. FIGS. 5 and 6 show the state where the table stage 111 is attached.

Further, as described above, in the present embodiment, the shape formed by cutting off the uppermost portion of the main body housing 100 along the rearward inclined plane is adopted and, in order to make use of the feature of the quarter circle shaped appearance, the housing handle section 102 is formed on the extension line of the quarter circle shape at the upper portion of the main body housing 100. The housing handle section 102 includes a pair of the supports 105 formed on both the sides of the device allocation plane 103 and a bar-shaped grip 104 connecting the paired supports 105 to each other at the uppermost portions. In the present embodiment, by installing the large housing handle section 102 at the upper portion of the main body housing 100, it is possible to impress the main body housing 100 of the quarter circle shape and improve the design flexibility and, by using the large housing handle section 102, it is possible to make it easy to indicate the moving direction of the universal wheels 101 and improve the mobility.

Further, in the present embodiment, it is possible to form a space 115 located above the inclined plane 114 and surrounded by the paired supports 105 and the bar-shaped grip 104. The space 115 makes it possible to reduce the feeling of pressure imposed on an operator holding the housing handle section 102. Furthermore, during the transfer of the ultrasonograph 1, an operator can hold the supports 105 in addition to the bar-shaped grip 104 and hence it is possible to facilitate the operation in the revolving and straight forwarding of the ultrasonograph 1 with the universal wheels 101.

Further, in the present embodiment, it is possible to make use of the space 115 as the fourth device container. In order to realize the fourth device container, in the present embodiment, the bar-shaped grip 104 is supported by the supports 105 at the position extending rearward from the back face of the main body housing 100 as shown in FIG. 5(d). By the configuration, it is possible to maintain the main function as the housing handle section 102 even when the space 115 is used as the fourth device container.

Here, the structure for folding the table 107 is explained in reference to FIG. 7. The table 107 is foldably connected on both the sides at the front portion with connection hinges 117 formed on both the sides at the front portion of the inclined plane 114 so that the table 107 may be stored in the table container 116 formed on the inclined plane 114. An extractable support 118 is installed in the table container 116. By this configuration, the table face 108 is at the same level as the housing face around the table container 116 and thus the table 107 is store in a compact manner in the state where the table 107 is stored in the table container 116 and the table face 108 can be maintained horizontally with the paired connection hinges 117 and the support 118 in the state where the table 107 is extracted.

Then in the present embodiment, the connection hinges 117 are structured so as to be attachable and detachable and it is possible to attach the table stage 111 by using the table container 116 as the positioning means as shown in FIGS. 5 and 6 in the state where the table 107 is detached. In the present embodiment, it is possible to: use the table 107 when it is used as a space for disposing small goods of light weight; and attach the table stage 111 when the auxiliary device 59 of a heavy weight as shown in FIG. 5 is disposed. In addition, when the table 107 is adopted, the table 107 is attached to a position lower than the uppermost positions of the arc supports 105 and hence the supports 105 and bar-shaped grip 104 surrounding the table face 108 function as a safety bumper.

In FIG. 5 again, when the table stage 111 is attached in contrast, the table face 108 is supported so that the table face 108 may form a horizontal plane extending forward from the uppermost portions of the arc supports 105. By so doing, the supports 105 and the bar-shaped grip 104 do not interfered with the switches and cords of various devices disposed on the table face 108 and hence it is possible to use the fourth device container effectively.

Further, the supports 105 are formed in the manner of extending on both the sides of the device allocation plane 103 in conformity with the arc shape. In the present embodiment, probe containers 110 are formed at one of the supports 105 formed on both the sides of the device allocation plane 103. The probe containers 110 include a plurality of through-holes vertically piercing and being notched at one side and the through-holes are formed so as to be aligned in the longitudinal direction of the supports 105. By so doing, the ultrasonic probes stored in the plurality of probe containers 110 are not lapped vertically and anteroposteriorly and hence are easily attached and detached.

Furthermore, the supports 105 are formed in the manner of protruding in the transverse direction and thereby have the function of a bumper to absorb impact imposed from both the sides of the main body housing 100. Moreover, the recesses 226 are formed on both the side plates of the main body housing 100 in the vicinity of the supports 105 and hence the storage space of the ultrasonic probes 58 is secured when the probe containers 110 formed at the supports 105 are mounted and the handling of the ultrasonic probes 58 can be improved.

Further, as shown in FIG. 6(a), an openable lid 227 used for mounting and maintaining various kinds of devices such as the second device container 71 and the third device container 72 disposed in the main body housing 100 is installed at the back face of the main body housing 100.

In FIG. 5 again, the operation device 200 includes: the first housing 201 of a half-track type the front portion of which has an arc shape; the second housing 202 foldably attached through the operation connector 204; a bumper section 205 formed around the first housing 201; and the keyboard 210 (refer to FIG. 12) not shown in the figure stored in the bottom face portion of the first housing 201. A protrusion 211 protruding upward is formed at the rear end of the upper face of the first housing 201 and the operation connector 204 is formed in the center of the protrusion 211 and a speaker net 212 incorporating a speaker section is formed on both the sides of the operation connector 204 (refer to FIG. 12(a)).

As shown in FIGS. 8 and 9, in the present embodiment, the second housing 202 is foldable and revolvable by installing the operation connector 204 at the protrusion 211. Further, as shown in FIG. 12(a), by disposing the speaker net 212 on the inclined face of the protrusion 204 facing the side of an operator, it is possible to obtain acoustic effect having directivity.

In FIGS. 8 and 9 again, the bumper section 205 is formed in the manner of extending forward from the top ends on both the sides of the protrusion 204. Then the sum of the width of the first housing 201 and the width of the bumper section 205 on both the sides is set so as to coincide with the width of the second housing 202. Consequently, in the state where the second housing 202 is opened, both the ends of the bumper section 205 coincide with the width of the second housing 202 and also the rear end portion of the bumper section 205 lies next to the bottom end of the second housing 202, and hence the bumper section 205 formed on both the sides of the first housing 201 and the second housing 202 appear to be united and hence the design flexibility improves. Moreover, the width of the second housing 202 can be increased and hence it is possible to adopt a large monitor screen 203.

Further, as shown in FIG. 8, the bumper section 205 is formed in the manner of extending forward along both the sides of the first housing 201 and continues to the arched grip 209 located at the front portion of the first housing 201 while the width in the vicinity of the protrusion 211 is maintained. Then in the state where the second housing 202 is folded, the height of the second housing 202 is set so that the front end portion thereof may coincide with the front end portion of the first housing 201. As a result, in the state where the second housing 202 is folded, the bumper section 205 except the arched grip 209 located at the front portion of the first housing 201 can be contained within the projected area of the second housing 202.

On the other hand, as shown in FIGS. 9 and 10, both the side portions of the bumper section 205 are formed so as to: gradually descend toward the front from the uppermost portion of the protrusion 211; come to a position lower than the bottom face of the first housing 201 from the vicinities of the center portions on both the sides of the first housing 201; and be parallel with the bottom face of the first housing 201 from the position. As a result, the bumper storage space 213 having the thickness H2 of the first housing 201 is secured at the front portions on both the sides of the bumper section 205. In the present embodiment, the jelly container storage section 228 and the second probe container 229 are formed in the bumper storage space 213. Here, the second probe container 229 is formed so as to have the same structure (shape) as the probe containers 110.

In this way, the bumper storage space 213 is secured as a storage space regardless of whether the second housing 202 is opened or closed. Then the bumper storage space 213 is located at a place closest to an operator in the state where the second housing 202 is opened and hence it is possible to store the frequently used in-use ultrasonic probes 58 and jelly container 83.

As stated above, by the operation device 200 according to the present embodiment, in the state where the second housing 202 is opened, the operation switches 400 and the monitor screen 203 are closely disposed and moreover the in-use ultrasonic probes 58 and jelly container 83 are stored on both the sides of the operation switches 400, and hence usability is improved. Further, the operation device 200 can be moved to an arbitrary position from an operator by being moved or rotated with the arched grip 209. In the state where the second housing 202 is closed in contrast, it is possible to hide the operation switches 400, the monitor screen 203, and the in-use ultrasonic probes 58 and jelly container 83 with the second housing 202 and hence it is possible to secure the roominess and protect the devices against external obstacles and dust.

Successively, the operation connector 204 that makes it possible for the second housing 202 to be folded and revolved is explained in detail in reference to FIG. 11. The operation connector 204 according to the present embodiment includes: a concave rotary support section 214 formed at the protrusion 211; a convex foldable connecting shaft section 215 formed at the second housing 202; and an intermediate joint section 216 to connect the rotary support section 214 to the foldable connecting shaft section 215. The intermediate joint section 216 has a rotary shaft 217 rotatably attached to the rotary support section 214 at the bottom face and a concave foldable connecting bearing section 218 that engages with the foldable connecting shaft section 215 is formed on the upper face.

The concave rotary support section 214 is formed in the manner of securing a sufficient clearance for rotating the rotary joint section 216 in the Z4 direction around the rotation axis P4 when the intermediate joint section 216 is attached through the rotary shaft 217. Further, the intermediate joint section 216 is formed in the manner of having a side face shape continuing from the protrusion 211 on both the sides when the intermediate joint section 216 is attached to the rotary support section 214. Furthermore, the foldable connecting shaft section 215 has rotary shafts 219 on both the sides and the second housing 202 can be folded around the rotation axis P3 by engaging the rotary shafts 219 with rotary bearings 220 formed on both the sides of the rotary support section 214. Here, in the present embodiment, each of the rotary shaft 217 and the rotary shafts 219 is formed into a hollow shape and electrical wiring is laid between the first housing 201 and the second housing 202. By so doing, unsightly wiring is avoided.

In this way, the operation connector 204 according to the present embodiment: connects the first housing 201 to the second housing 202 through the intermediate connecting section 216; thereby makes it possible to form the rotation axis P3 and the rotation axis P4 intersecting with each other at right angles; and thereby makes it possible to realize the folding and revolving functions.

Successively in reference to FIG. 12, in the present embodiment, a keyboard storage section 221 to accommodate a keyboard 210 is formed at the bottom face portion of the first housing 201. The keyboard 210 has a thin tabular appearance and has the front portion having the shape of an arc in conformity with the front shape of the first housing 201. Then on the upper face of the keyboard 210, a keyboard group including a plurality of keys is allocated rearward and thereby a palm rest is secured at the front arc-shaped portion.

Meanwhile, the keyboard storage section 221 is formed in the manner of having a pair of support rails 222 to slidably support both the ends of the keyboard 210 on both the sides. Further, a connecting pin 223 is formed at the rear end on the upper face of the keyboard 210 and slidably connected to a slide groove 224 formed on the ceiling face of the keyboard storage section 221. By the configuration, the keyboard 210 is supported by the support rails 222 on both the sides and thereby can be accommodated in the keyboard storage section 221. When the keyboard 210 is used in contrast, the keyboard 210 can be extracted from the keyboard storage section 221 along the support rails 222. On this occasion, the connecting pin 223 also slides along the slide groove 224 and functions so that the keyboard 210 may not be extracted beyond a prescribed position where the keyboard group is exposed. By so doing, it is possible to prevent the keyboard 210 from falling.

Then by the keyboard extracting mechanism having the aforementioned structure, the extracted keyboard 210 is supported at the lower portion with the arched grip 209 and hence it is possible to securely hold the keyboard 210 against the stress imposed downward by the input operation while the wrists are placed on the palm rest of the keyboard 210 with the arched grip 209. Moreover, since the keyboard 210 can be rotated in the transverse direction around the connecting pin 223 by the connection between the connecting pin 223 and the slide groove 224, it is possible to secure the degree of freedom in the operation posture during input operation.

Successively, the operation switches 400 are explained further in detail in reference to FIG. 13. As described above, in the present embodiment, switches are allocated in the shape of an arc around the trackball 401. The trackball 401 is located in the vicinity of the center of the arc shape at the front portion of the first housing 201. In the present embodiment, the center of the arc shape is located on the rotation axis P2. Then when a straight line P10 is defined as the line that passes through the rotation axis P2 and intersects with the rotation axis P3 at right angles, the region opening fanwise from the rotation axis P2 toward the straight line P10 at the angle $\Theta 10$ is formed as a flat plane where keys and operation buttons are not disposed and the flat plane is used as the palm rest 208, and the other region of the angle $\Theta 11$ (360 degrees−$\Theta 10$) is used as the operation allocation plane where keys and operation buttons are disposed. Here, in the present embodiment, 810 is set at about 90 degrees in the manner of opening bilaterally symmetrically with respect to the straight line P10.

Further, a home position mark 230 including small protrusions is formed at the palm rest 208 on one side of the straight line P10. In the present embodiment, the home position mark 230 including three protrusions is formed in the vicinity of the marginal part on the right of the palm rest 208. By the configuration, it is possible to set the home line P13 on the basis of the two points; the home position mark 230 and the trackball 401.

An operator can operate various switches disposed on the circuits around the trackball 401 by touch typing by: positioning the vicinity of the left wrist on the home position mark 230 by tactile sense; touching the trackball 401 by the tactile sense of a finger tip; and thereby adjusting the left hand to operate the operation switches 400 to the home line P13 by touch typing. In the ultrasonograph 1, the above feature is effective because touch typing operation is frequently carried out in order to handle an ultrasonic probe 58 with a hand and operate the operation switches 400 with the other hand while watching the monitor screen 203.

Here, although the home position mark 230 is formed on the right side of the palm rest 208 in the present embodiment since the majority is generally right-handed (the ultrasonic probe 58 is operated with the right hand), the home position mark 230 may be formed also on the left side of the palm rest 208. Although the positional relation between the palm rest and a wrist is recognized by forming a small protrusion at the whole periphery of the palm rest 208 in a conventional technology, the feature of the present embodiment is that small protrusions are formed on one side or separately on both the sides of the palm rest 208 and used as the home position mark 230 and the home line P13 passing through the home position mark 230 and the trackball 401 is formed.

Successively, the operation switches 400 allocated around the trackball 401 are explained further. Firstly, as a first circular key group 410 closest to the trackball 401, an enter key 411, a cancel key 412, a pulsed Doppler exchange key 413, and a continuous Doppler exchange key 414, those being frequently used, are disposed. The first circular key group 410 is formed in the manner of identifiable from other key groups by forming into a continuous ring shape. Secondly, large round keys are aligned at equal intervals as a second circular key group 420 around the first circular key group 410. As the second circular key group 420, a freeze key 426, a B-mode key 425, a color mode key 424, a Doppler mode key 423, an M-mode key 422, and an ODM beam line key 421 are aligned. Here, the freeze key 426 employs a push button switch mechanism to light in an operation reception state, the keys other than the freeze key 426 in the second circular key group 420 employ a push button switch mechanism to light in the center in an operation reception state, and rings around them employ a rotary switch mechanism.

That is, as shown in FIG. 13(b), the ODM beam line key 421 or the like includes: an opening 421 having a ring-shaped recess 421g around the opening 421 on the first housing face 206; a push button switch mechanism 421e installed in the opening 421; a push button switch 421a mounted in the opening 421; a rotary ring 421b mounted in the recess 421g; and a rotation detector 421c installed at the recess 421g. In the present embodiment, the operation of pushing the push button switch 421a can be detected with the push button switch mechanism 421e and the rotation of the rotary ring 421b can be detected with the rotation detector 421c. Then the push button switch 421a and the rotary ring 421b are made of a transparent material and a lamp 421d is installed in the interior of the push button switch 421a, and hence, when the ODM beam line key 421 is operated, the lamp 421d lights and the light illuminates the push button switch 421a and the rotary ring 421b.

Further, around the second circular key group 420, a third circular key group 430 and a fourth circular key group 440 are disposed at the front portions on both the sides, a fifth circular key group 460 and a sixth circular key group 465 are disposed at the rear portions on both the sides, and a slide switch group 450 is further disposed at the rear portion on the right side. As the third circular key group 430, a first picture recording button, switches for print and screen change, and others are disposed. As the fourth circular key group 440, a second picture recording button, a measurement menu, a report switch, and others are disposed. As the slide switch group 450, a plurality of chromaticness-dependent gain slide switches are disposed. As the fifth circular key group 460, switches for changing focus, focus stage number, and display depth are disposed. As the sixth circular key group 465, a function switch and others are disposed.

Meanwhile, in the present embodiment, the switches constituting the operation switches 400 are classified by the frequency of use and the switches classified by the frequency of use are allocated on the concentric circles formed around the trackball 401 in accordance with the frequency of use. That is, the most frequently used switches are classified in the first circular key group 410 and the second most frequently used switches are classified in the second circular key group 420. Then in the switches allocated on an identical concentric circle, a more frequently used switch is disposed on the right side, namely is disposed in the region P14 around the home line P13 in a biased manner.

In other words, in the operation switches 400 according to the present embodiment, the switches are disposed concentrically around the trackball 401 in accordance with the frequency of use and, in the concentrically disposed switches, a more frequently used switch is disposed on the side where the home position mark 230 is formed. By the configuration, it is possible for an operator to carry out various kinds of operations rapidly and moreover by touch typing since the operator can adjust a hand to the home line P13 and frequently used switches are disposed in the range that the hand can reach. Further, since the operation device 200 rotates around the trackball 401, the usage environment of an operator does not change largely even when the operator changes the position to the ultrasonograph 1. Hence it is possible to reduce the possibility of an operator's forced uncomfortable posture and the large change of touch typing operability. Moreover, the operator device 200 can move also in the vertical and transverse directions and hence it is possible to reduce the large change of the operation environment.

Furthermore, in the present embodiment, each of the operation switches 400 is structured so as to light when it receives an operation and hence an operator can understand the operation state at a glance. In the present embodiment in particular, the switches constituting the second circular key group 420 are aligned counterclockwise from the left in the order of operation and they are displayed and guided with a plurality of LED lamps 427 disposed concentrically, and hence the operability is further improved.

Successively, the operation mechanism of the movable arm 300 is explained in reference to FIGS. 14 and 15. FIG. 14 is a structural view of an elevating function mechanical section. FIG. 15 shows structural views of an attachment mechanical section; FIG. 15(a) is a transverse sectional view, FIG. 15(b)

is a vertical sectional view, and FIG. 15(c) is a front view in the state where the attachment mechanical section is moved to the transverse direction.

In FIG. 14, with the movable arm 300 according to the present embodiment, it is possible to take the first posture Q1 and the second posture Q2 while the position of the attachment mechanical section 350 attached to the tip thereof is maintained by adopting the elevating function mechanical section 301 having a link mechanism. In the present embodiment, in order to realize the structure, the elevating function mechanical section 301 includes: a first base section 310 attached fixedly to the main body housing 100; a second base section 311 to which the attachment mechanical section 350 is fixed; a pair of arm members 312 attached in parallel between the first base section 310 and the second base section 311; and a spring member 313 to connect an arm member 312 to a prescribed portion of the first base section 310.

An end of a first arm member 312a and an end of a second arm member 312b, the first arm member 312a and the second arm member 312b constituting the arm members 312, are rotatably attached to the first base section 310 at a rotation axis P1a and a rotation axis P1b, respectively. The other ends of the first arm member 312a and the second arm member 312b are rotatably attached to the second base section 311 at a rotation axis P5a and a rotation axis P5b, respectively. The length L1a between the rotation axes P1a and P5a of the first arm member 312a and the length L1b between the rotation axes P1b and P5b of the second arm member 312b are set to be identical and the length L2a between the rotation axes P1a and P1b and the length L2b between the rotation axes P5a and P5b are also set to be identical.

By the link mechanism, the rotary axis P5 virtually formed between the rotary axis P1b and the rotary axis P5b travels along the circle having the radius L1a (Lib) around the rotary axis P1 virtually formed between the rotary axis P1a and the rotary axis P1b. Then the attachment mechanical section 350 attached to the virtually formed rotation axis P5 rotates around the rotation axis P1 always in an identical posture.

Here, the movable arm 300 always wants to rotate downward by the weight (gravity G) of the operation device 200 attached to the tip thereof through the attachment mechanical section 350. Consequently in the present embodiment, a spring member 313 having the function of compensating the downward gravity G is installed. The spring member 313 is, for example, attached so as to: connect the second arm member 312b to the first base section 310; have a stress to cope with the gravity G; and always maintain the same position.

Further, although it is not shown in FIG. 14, in the present embodiment, it is possible to install a lock switch to fix the rotation of the movable arm 300. The lock switch is installed inside the arched grip 209 and the lock switch is unlocked when a user grasps the arched grip 209 and the lock switch is activated by releasing the grasp. The lock switch is structured so that the operation of the lock switch may be transferred to a fixing means not shown in the figure to fix the rotation of the rotation axis P5 (P5a, P5b) through a transfer means not shown in the figure.

By the configuration, a user moves the operation device 200 to an intended position while grasping the arched grip 209 and releases the arched grip 209 at the moved position, and thereby it is possible to fix the operation device 200 at an arbitrary position.

Successively, the concrete structure of the attachment mechanical section 350 is further explained in reference to FIG. 15. In FIG. 15, the attachment mechanical section 350 according to the present embodiment includes: a second base section 311 installed at the front end of the movable arm 300; an attaching base 320 attached through a rotation axis P6; a transfer base 321 slidably attached to the attaching base 320; and a rotation base 322 rotatably attached to the transfer base 321 through the rotation axis P2.

The attaching base 320 constitutes a tilt mechanical section 370 together with the second base section 311 and the rotation axis P6. The rotation axis P6 includes a screw or the like that can easily adjust the strength for tightening the joint between the attaching base 320 and the second base section 311 and it is possible to: fix the attaching base 320 and the second base section 311 by tightening the screw or the like; or fix them by tightening again after releasing the tightening and adjusting the angle to an arbitrary angle.

In the transfer base 321, a recess 361 having the same size as the width of the operation device 200 is formed at the bottom face section and transfer rails 362 are formed on both the sides (in Z5 direction) of the recess 361. Meanwhile, in the attaching base 320, rail attaching sections 363 that slidably engage with the transfer rails 362 are formed on both the sides (in Z5 direction). That is, in the present embodiment, the attaching base 320 engages with the recess 361 of the transfer base 321 and the horizontal movement mechanical section 360 is configured by the engagement of the transfer rails 362 and the rail attaching sections 363.

As shown in FIG. 15(a), in the present embodiment, the Z5 direction is set at the transverse direction of the ultrasonograph 1 and hence the transfer rails 362 are disposed horizontally in the transverse direction. In the present embodiment, since the operation device 200 is located within the projected area above the device allocation plane 103 in the normal state, the attachment mechanical section 350 having the transfer rails 362 having the size almost identical to the width of the device allocation plane 103 is disposed on a position above the device allocation plane 103.

In the normal state, the attaching base 320 attached to the tip of the movable arm 300 protruding upward from the arm transfer groove 109 disposed on one side of the device allocation plane 103 is attached to one side (the right side in the figure) of the transfer rails 362. From the state, by slidably moving the transfer base 321 in the Z5 direction (the right direction in the figure) relative to the rail attaching section 363 through the transfer rails 362, it is possible to take a third posture Q3 wherein the rail attaching section 363 shifts to the other side (the left side in the figure) of the transfer rails 362 as shown in FIG. 15(c).

In this way, in the present embodiment, it is possible to take the third posture Q3 wherein the operation device 200 hangs over on one side of the main body housing 100 from the ordinary first posture Q1 or second posture Q2 wherein the operation device 200 is located above the device allocation plane 103. The third posture Q3 wherein the operation device 200 hangs over on one side can accommodate various examination postures in a narrow patient's room or an examination room.

Further, as shown in FIG. 15(b), the operation device 200 is attached to the upper face of the rotation base 322 and the bottom face of the rotation base 322 is rotatably attached to the upper face of the transfer base 321 through the rotation axis P2 in the rotation mechanical section 380. In the present embodiment, a through-hole of the transfer base 321, a bearing formed at the rotation base 322, and a screw attached to the bearing through the through-hole constitute the rotation mechanical section 380.

In the present embodiment, an operator can direct the operation device 200 to an intended direction through the rotation mechanical section 380 even though the operation device 200 takes any of the first posture Q1, the second posture Q2, and the third posture Q3. Here, although the rotation base 322 is installed and the operation device 200 is attached to the rotation base 322 in the present embodiment, it is also possible to eliminate the rotation base 322, install the aforementioned bearing on the bottom face of the operation device 200, and attach a screw directly to the bearing through the aforementioned through-hole.

Next, the operation postures of the ultrasonograph 1 are further explained in reference to FIGS. 1 and 16. FIG. 16 shows views showing the states of operation postures when the ultrasonograph is used; FIG. 16(a) is a view showing the state of use with a standing posture, FIG. 16(b) a view showing the state of use with a sitting posture, and FIG. 16(c) a view showing the state of use where the operation device is extracted in the transverse direction.

Firstly in FIG. 1, in the present embodiment, it is convenient to take the first posture Q1 wherein the tip of the movable arm 300 is located at an upper position and the second housing 202 is folded in the storage of the ultrasonograph 1. The first posture Q1 is the state where the operation device 200 is contained within the projected area of the main body housing 100 and is located at the uppermost position of the main body housing 100. Consequently, in the first posture Q1 as the storage state, the installation area is smallest, the part overhanging to the circumference is also small, moreover the operation switches 400 and the monitor screen 203 are hidden, and hence the roominess is good.

An operator can move the ultrasonograph 1 to an arbitrary place from the storage state by holding the large housing handle section 102. On this occasion, the ultrasonograph 1 is excellent in rotatability and linearity because of the same reasons as in the storage state.

Further, when the second housing 202 is opened in the state where the ultrasonograph 1 is moved to an intended examination site, the monitor screen 203 and the operation switches 400 can be brought in the state of stand-by only one operation. In the present embodiment, by installing an electric power switch and a breaker switch not shown in the figure on the housing face of the main body housing 100 and turning on the switches, it is possible to make the ultrasonograph 1 in the state of turn-on and display the activation and start-up screen not shown in the figure on the monitor screen 203. Then it is possible to carry out various examinations by operating the operation switches 400.

In the state of the turn-on, it is possible to set: the jelly container 83 in the jelly container storage section 228 formed at the bumper section 205; and a used ultrasonic probe 58 in the second probe container 229. Consequently, good readiness is obtained. Further, a spare ultrasonic probe 58 and a spare jelly container 83 can be stored in a probe container 110 and the container storage recess 113 and hence backup is also secured.

Then as shown in FIG. 16(a), the first posture Q1 wherein the operation device 200 is set at an upper position of the main body housing 100 is effective when an operator operates in a standing posture. From the standing posture, when the operation device 200 is lowered by handling the arched grip 209 and the second posture Q2 shown in FIG. 16(b) is taken, an operation posture most appropriate for a sitting posture is obtained. The second posture Q2 is a posture that facilitates sitting operation by an operator since the operation device 200 is set at a lower position in the manner of extending forward.

By the second posture Q2, for example, an operator can carry out examination by: sitting on a chair; holding an ultrasonic probe 58 with the right hand; operating the operation switches 400 with the left hand; and directing the line of sight to the monitor screen 203. In the sitting posture, the knees of the operator can be located under the operation device 200 and hence it is possible to move the main body housing 100 closer to the operator.

Then in the examination state, the operation device 200 can be revolved in the manner of shaking the head and hence it is possible to adjust the monitor screen 203 and the operation switches 400 to positions good for the visibility and the operability in conformity with the operator's posture. Moreover, the operator can operate the operation switches 400 by touch typing by adjusting the left hand to the home line P13. Further, since the ultrasonic probes 58 and the jelly container 83 are attached to the operation device 200, the examination with the ultrasonic probes 58 is facilitated.

Further, from the second posture Q2, it is possible to take the third posture Q3 shown in FIG. 16(c) wherein the second housing 202 is extracted to a side of the main body housing 100 when the operation device 200 is moved close to a bed or the monitor screen 203 is shown to an examinee. By the third posture Q3, when the space next to a bed is small for example, it is possible to: insert the ultrasonograph 1 in the space so that the longitudinal direction thereof may be parallel with the longitudinal direction of the bed; and carry out examination in the posture wherein the operator is positioned between the bed and the ultrasonograph 1. Further, it is advantageous also when the ultrasonograph 1 cannot be placed near the bed or when it is desirable to place the operation device 200 above the bed.

In this way, in the present embodiment, since the second housing 202 having the monitor screen 203 is installed foldably and rotatably to the first housing 201 having the operation switches 400, an operator can adjust the operation switches 400 in conformity with the posture of the hand for operation and separately adjust the monitor screen 203 to the line of sight of the operator. Then the operation device 200 can variously move by horizontal movement, tilt function, and rotation function, in addition to the elevating function, and hence it is possible to adjust the operation device 200 to the operation postures including the operability and visibility of an operator and information service to an examinee by simple operations.

Second Embodiment

Next, an ultrasonograph 1a according to the second embodiment is explained in reference to FIG. 17. FIG. 17 shows general structural views of an elevating function mechanism container of the ultrasonograph according to the second embodiment; FIG. 17(a) is a plan view in the first posture Q1, FIG. 17(b) a side view in the first posture Q1, FIG. 17(c) a plan view in the second posture Q2 or the third posture Q3, and FIG. 17(d) a side view in the second posture Q2 or the third posture Q3.

Firstly, in FIG. 17, in the present embodiment, a rearward inclined device allocation plane 103a is formed on the front face of a main body housing 100a and a structure to move an operation device 200 vertically along the inclined device allocation plane 103a is provided. An elevating function mechanical section 301a includes: an elevator section 340 installed in the main body housing 100a; horizontal arms 341 attached to the elevator section 340; a slide table 342 attached to the horizontal arms 341 slidably in the anteroposterior direction (the direction indicated with the arrow P20); slide grooves 343 installed on both the sides of the device allocation plane 103a; and an attachment mechanical section 350a attached rotatably and slidably to the slide table 342.

In the present embodiment, when the elevator section 340 moves vertically, a pair of horizontal arms 341 attached to the elevator section 340 moves vertically while the horizontality is maintained. Rollers 344 moving along the slide grooves 343 are attached to both the sides at an end of the slide table 342. Consequently, when the horizontal arms 341 move vertically, the slide table 342 moves to the anteroposterior direction (the direction indicated with the arrow P20).

That is, in the present embodiment, as shown in FIGS. 17(a) and 17(b), the state where the horizontal arms 341 are located at an upper portion of the inclined device allocation plane 103a means the first posture Q1 wherein the operation device 200 attached to the attachment mechanical section 350a is contained within the projected area of the main body housing 100a. When the horizontal arms 341 descend from the first posture Q1 through the elevator section 340, the rollers 344 attached to an end of the slide table 342 move downward along the slide grooves 343 formed in the manner of inclining along the device allocation plane 103a. Since the slide table 342 is slidably supported with the horizontal arms 341, the slide table 342 also descends when the horizontal arms 341 descend.

The descending slide table 342 descends while being pushed out (in the direction shown with the arrow P20) by the engagement between the rollers 344 and the slide grooves 343, and the operation device 200 takes the second posture Q2 wherein the operation device 200 hangs over in the direction shown with the arrow P20 at a lower portion of the inclined device allocation plane 103a as shown in FIGS. 17(c) and 17(d). In contrast, when the horizontal arms 341 are pulled upward through the elevator section 340, the slide table 342 ascends while being retracted toward the side of the main body housing 100a by the engagement between the slide grooves 343 and the rollers 344, and hence the operation device 200 can take the first posture Q1 as shown in FIGS. 17(a) and 17(b).

Although a paired structure wherein the horizontal arms 341 are supported on both the sides of the device allocation plane 103a is adopted in the embodiment shown in FIG. 17, it is also possible to adopt a one-side support structure like in the first embodiment. Further, the connector devices 51 explained in FIG. 4 are disposed on the device allocation plane 103a although they are not shown in FIG. 17.

In this way, in the second embodiment, it is possible to take the first posture Q1 and the second posture Q2 without using a link mechanism while the posture of the operation device 200 is maintained and hence the functional effects similar to those in the first embodiment can be obtained.

Other Embodiments

Although the control section 53 is installed in the main body housing 100 in the aforementioned embodiments, it is also possible to install it in the operation device 200.

Further, as another embodiment, the arm transfer groove 109 may be structured so as to be covered with an accordion-type cover. For example, it is possible to avoid the intrusion of foreign matters into the arm transfer groove 109 by: installing an expansive accordion-type cover for connecting the top end of the arm transfer groove 109 to the movable arm 300 and the movable arm 300 to the bottom end of the arm transfer groove 109, respectively; and covering the opening of the arm transfer groove 109 accompanying the transfer of the arm transfer groove 109.

Further, it is also possible to install a heat dissipation port on an inclined plane 114 formed rearward on the upper face of the main body housing 100. On this occasion, the heat dissipation port may be opened or closed by forming the heat dissipation port at the table container and opening or closing the table 107. On this occasion, it is also possible to form another heat dissipation port at the outer circumference and a path to communicate between another heat dissipation port and the aforementioned heat dissipation port in the table stage 111.

EXPLANATION OF REFERENCE NUMERALS AND SYMBOLS

Figure 1:
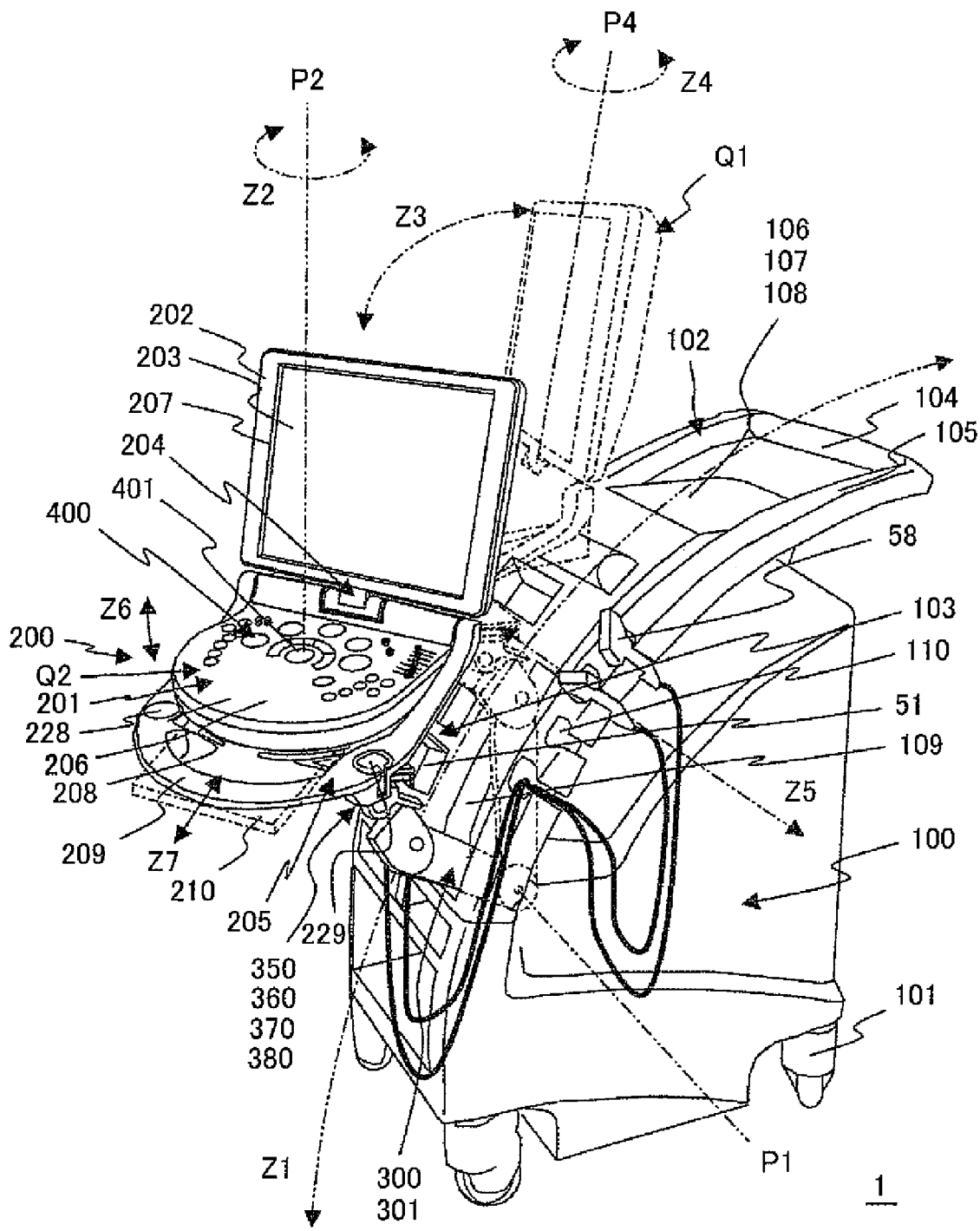
FIG. 1 is a perspective view showing a general structure of an ultrasonograph according to the first embodiment.
Figure 2:
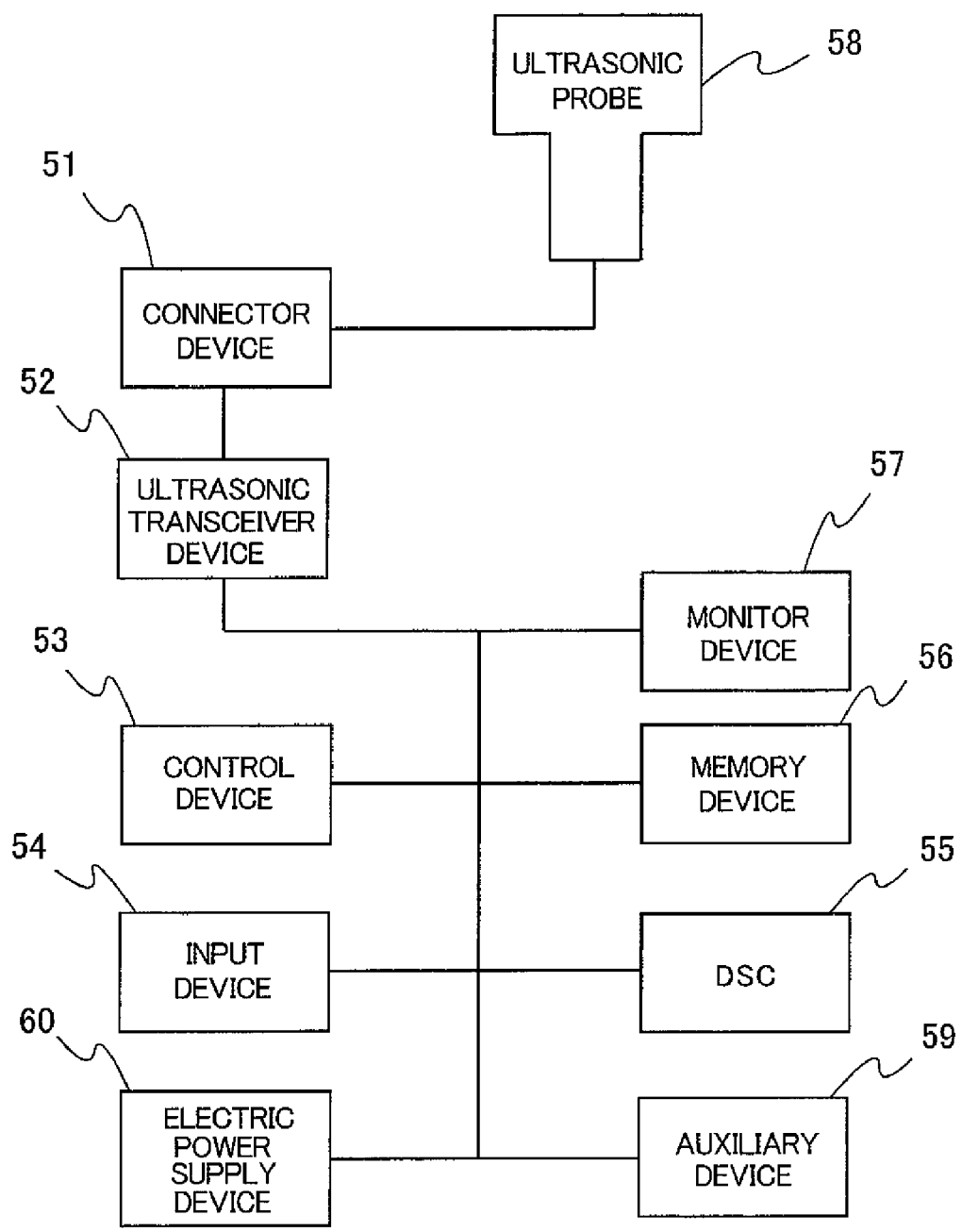
FIG. 2 is a block diagram of an ultrasonograph.
Figure 3:
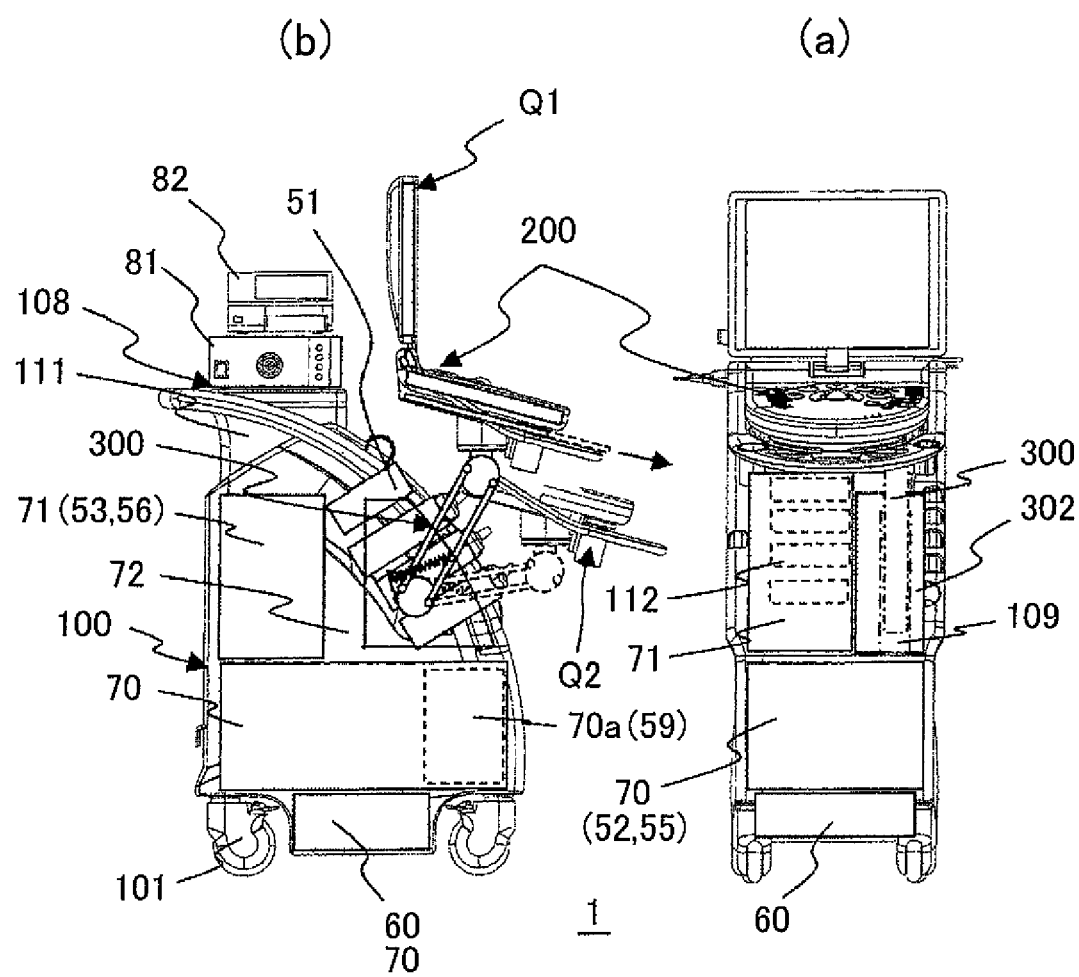
FIG. 3 shows conceptual views showing the configuration of each device in an ultrasonograph.
Figure 4:
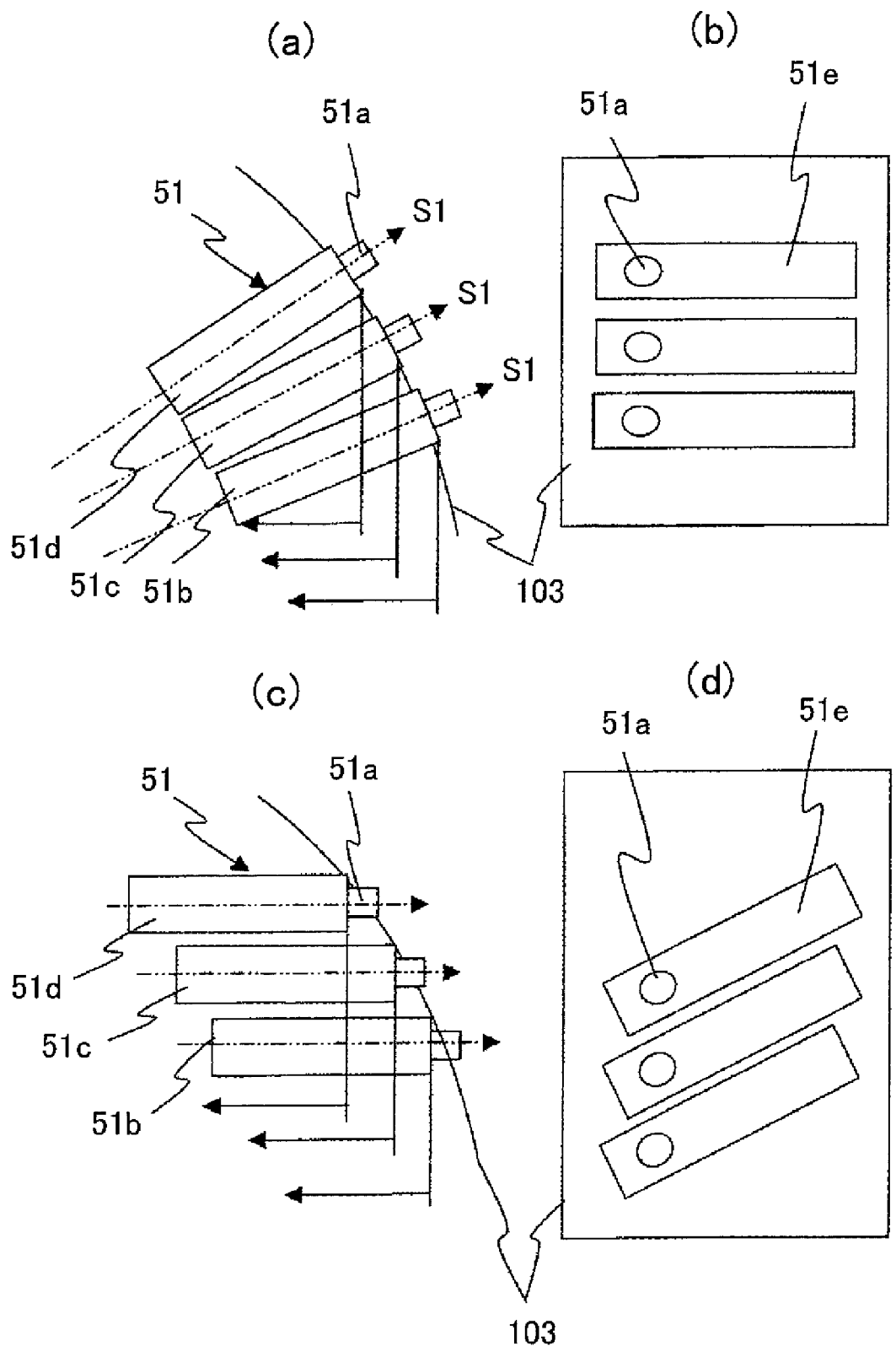
FIG. 4 shows views showing device allocation on a device allocation plane.
Figure 5:
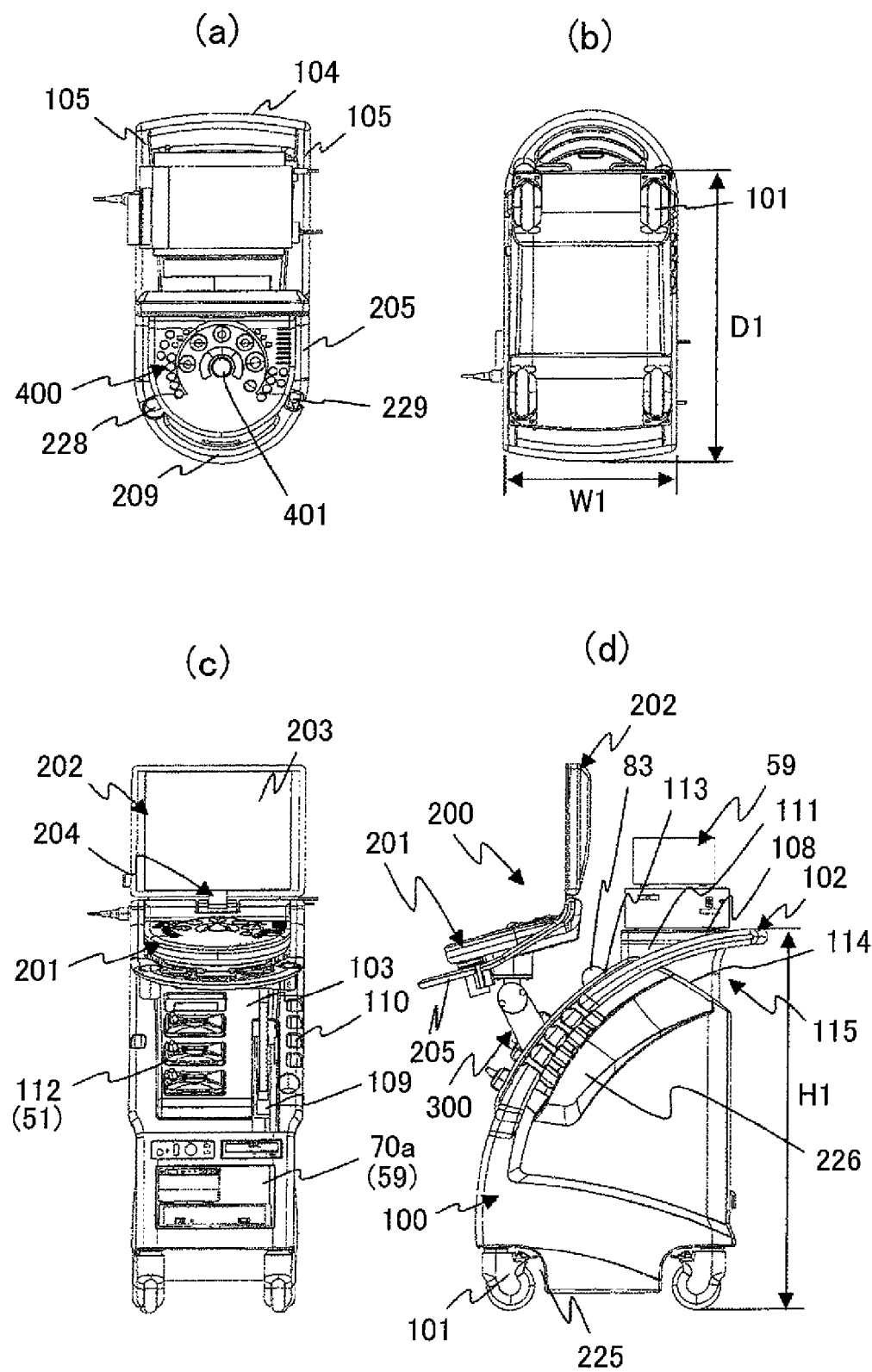
FIG. 5 shows external views of the ultrasonograph 1.
Figure 6:
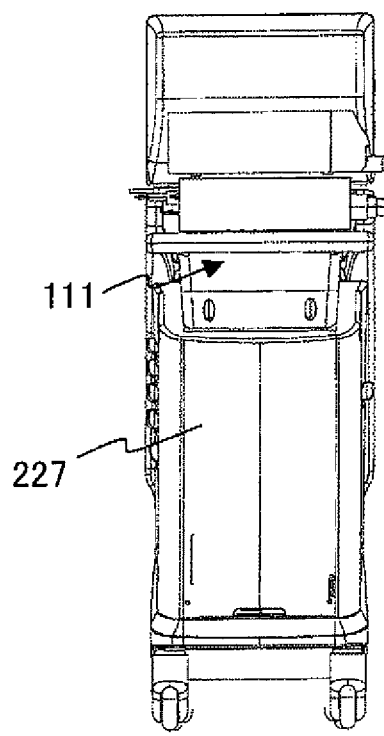
FIG. 6 shows external views of the ultrasonograph 1.
Figure 6:
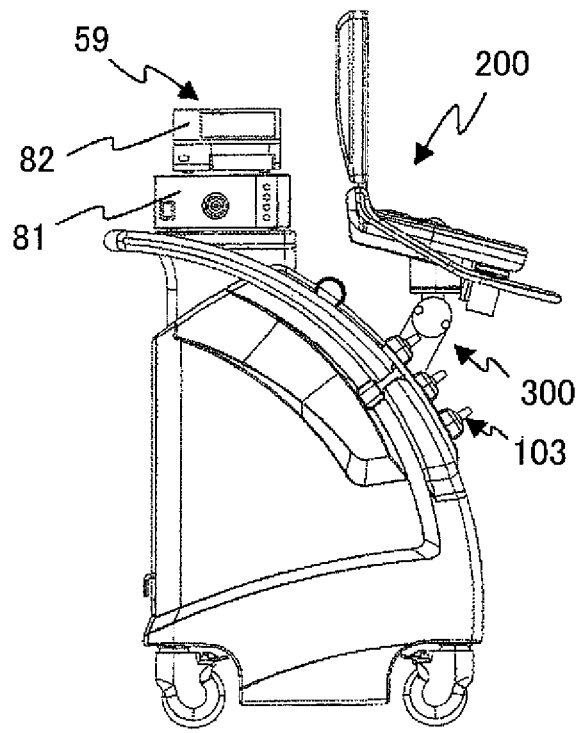
Figure 6:
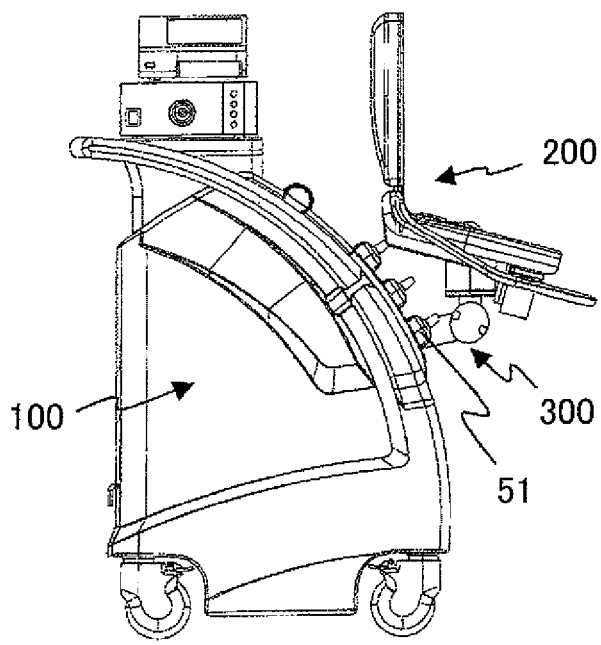
Figure 7:
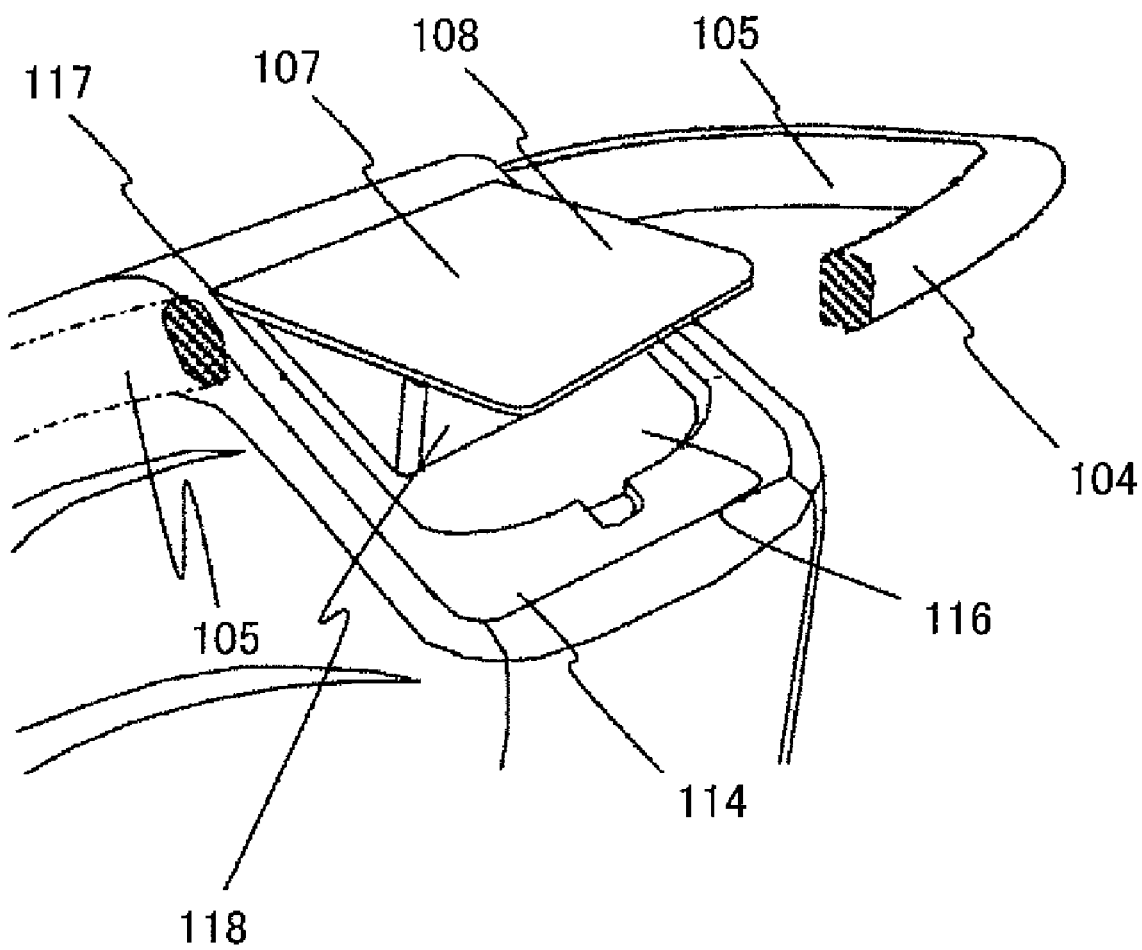
FIG. 7 is a perspective view showing the folding structure of a table.
Figure 8:
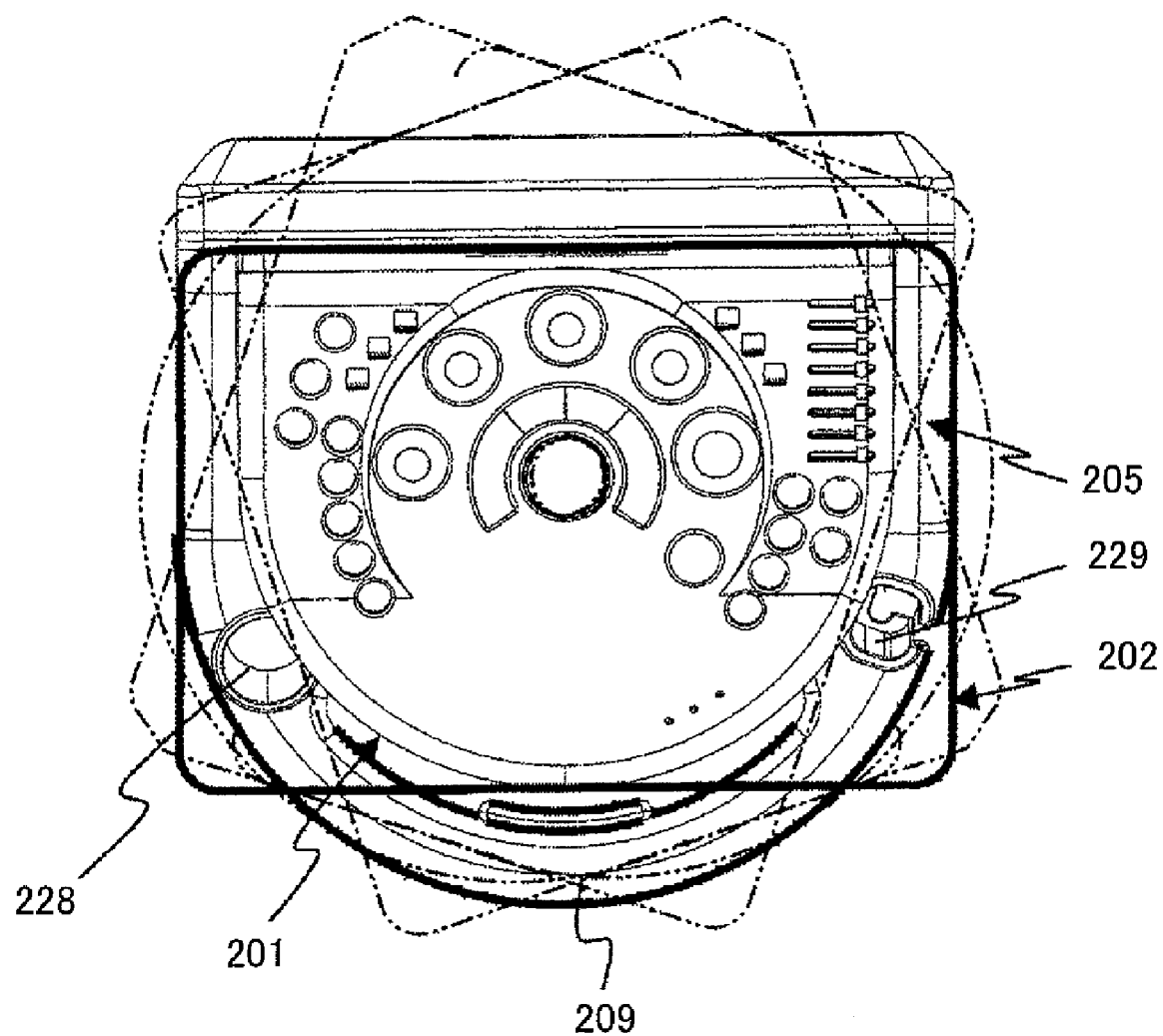
FIG. 8 is a plan view of an operation device.
Figure 9:
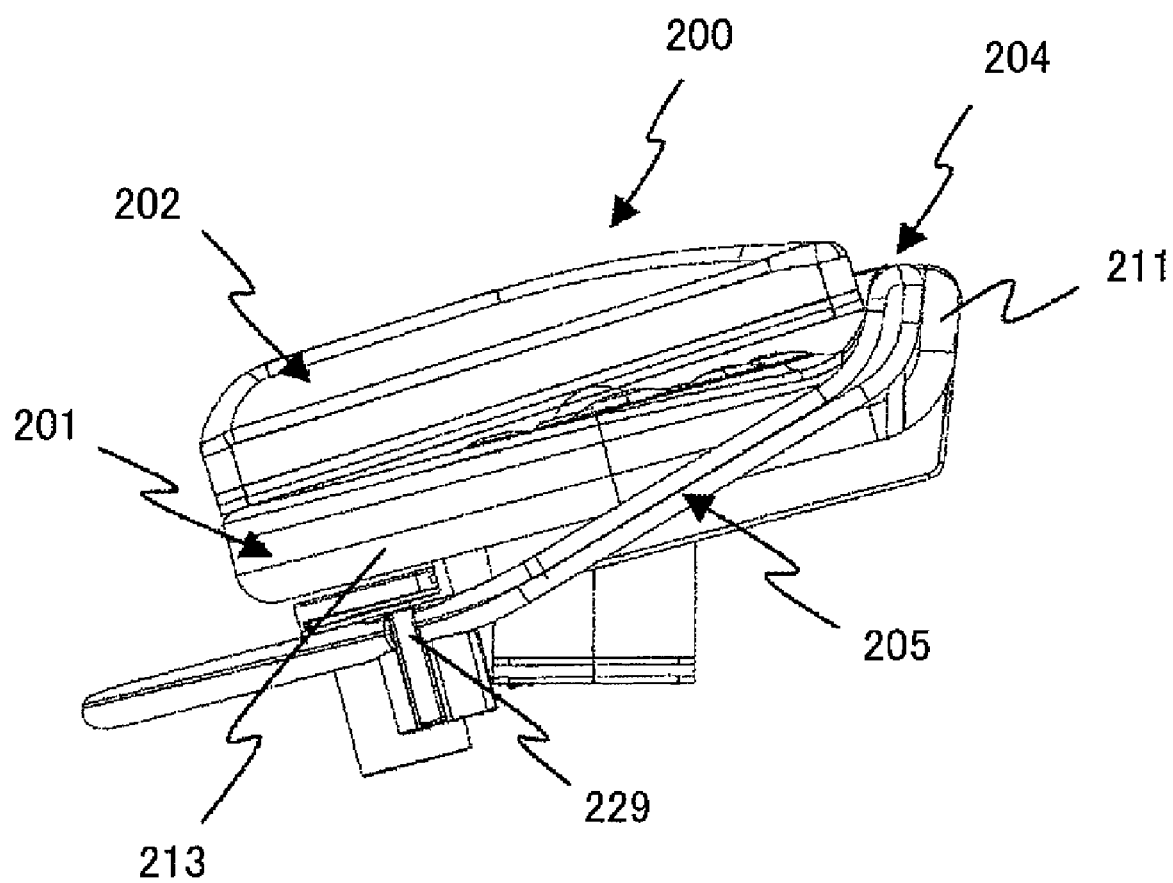
FIG. 9 is a right side view of the operation device in the state where the second housing is closed.
Figure 10:
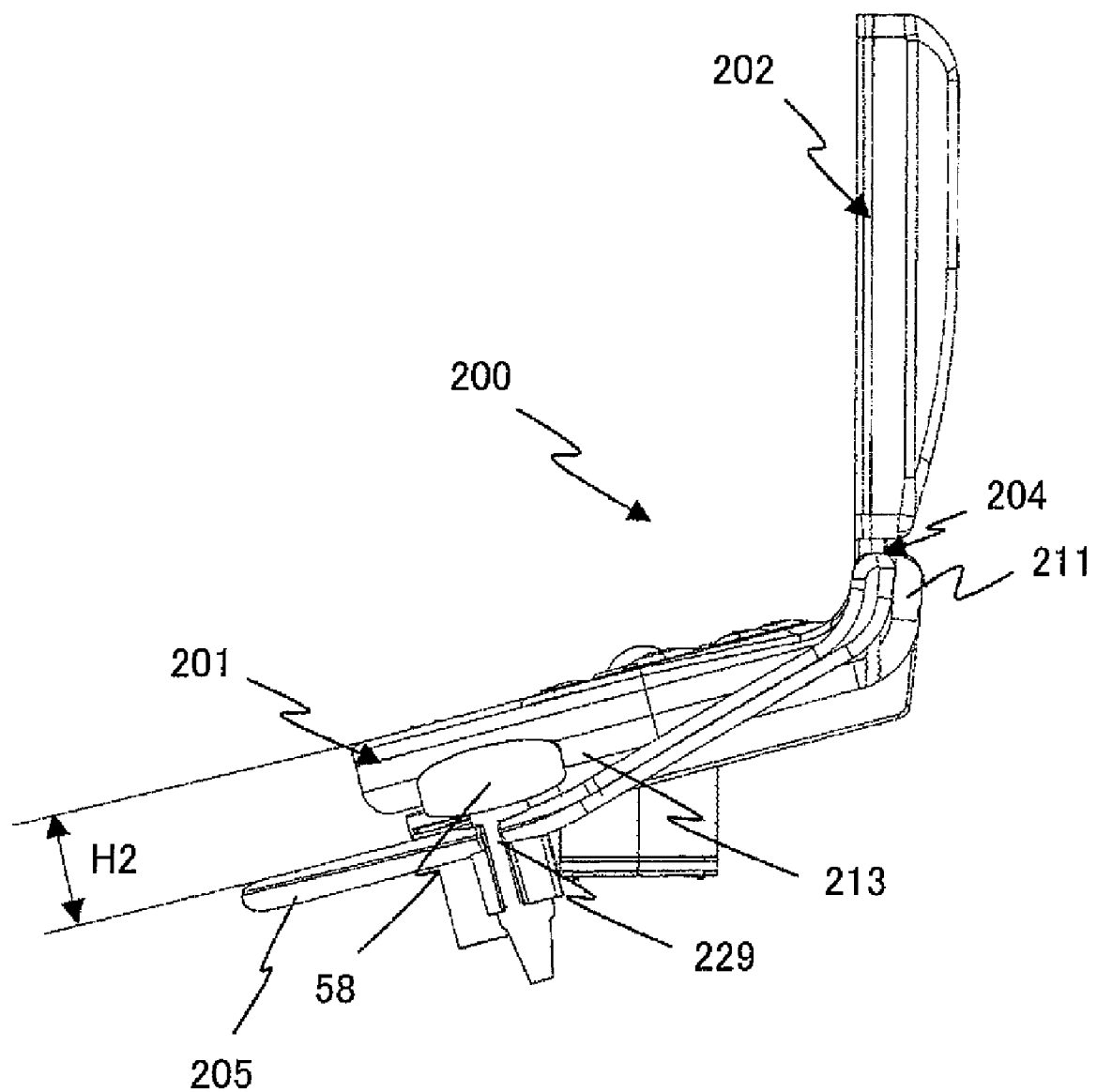
FIG. 10 is a right side view of the operation device in the state where the second housing is opened.
Figure 11:
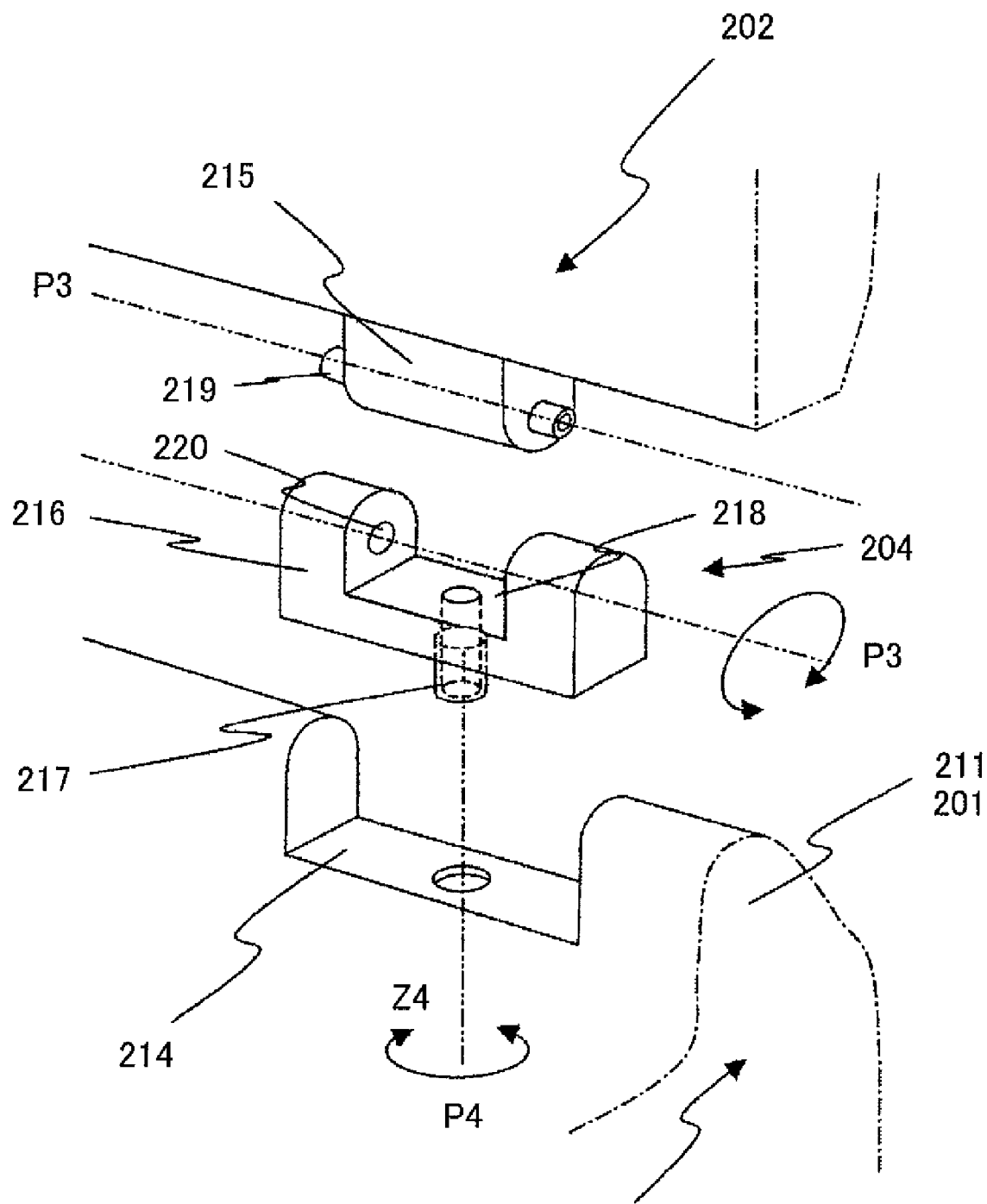
FIG. 11 is an exploded structural view of an operation connector.
Figure 12:
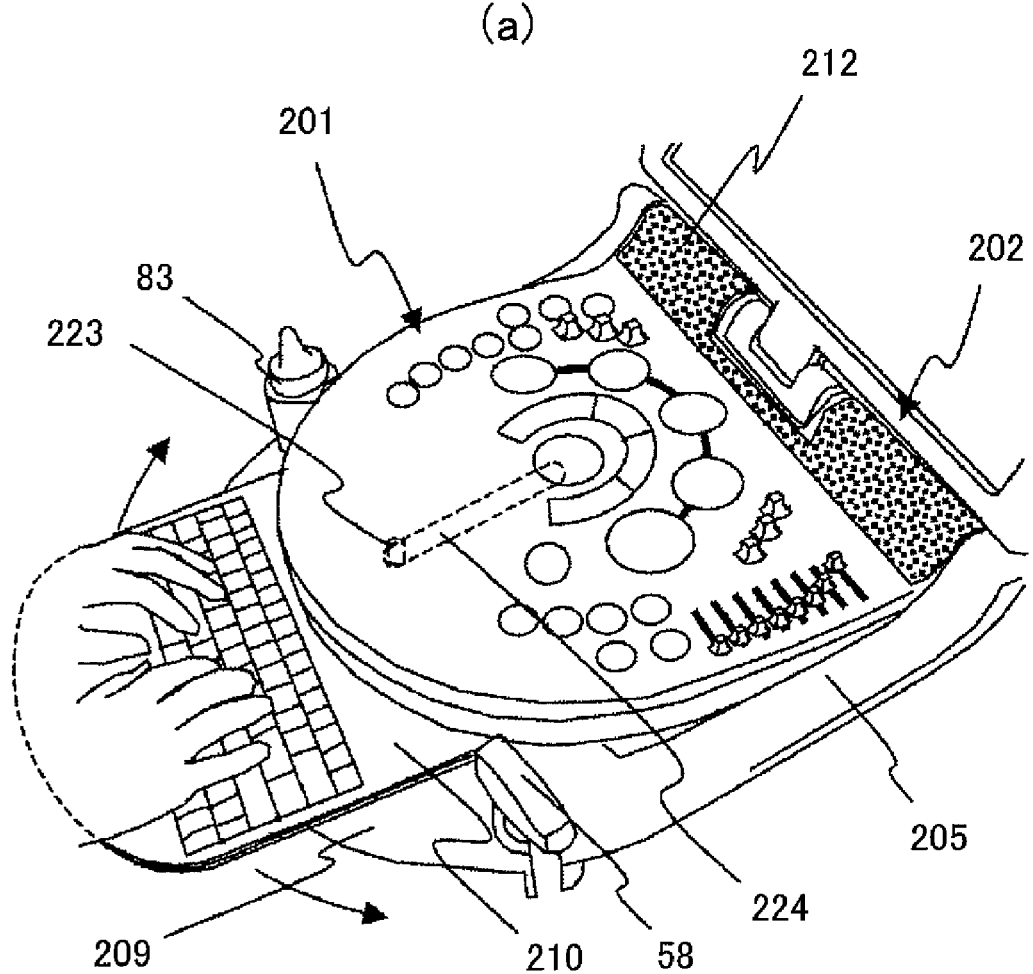
FIG. 12 shows external views in the state where a keyboard is extracted.
Figure 12:
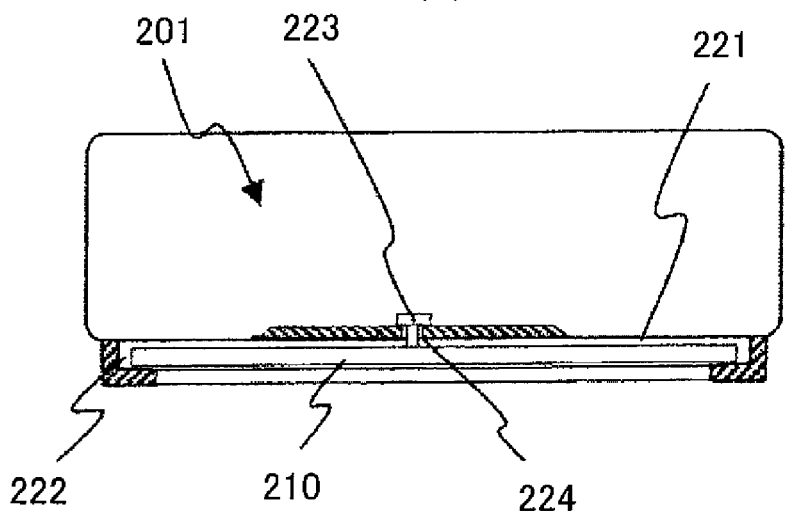
Figure 13:
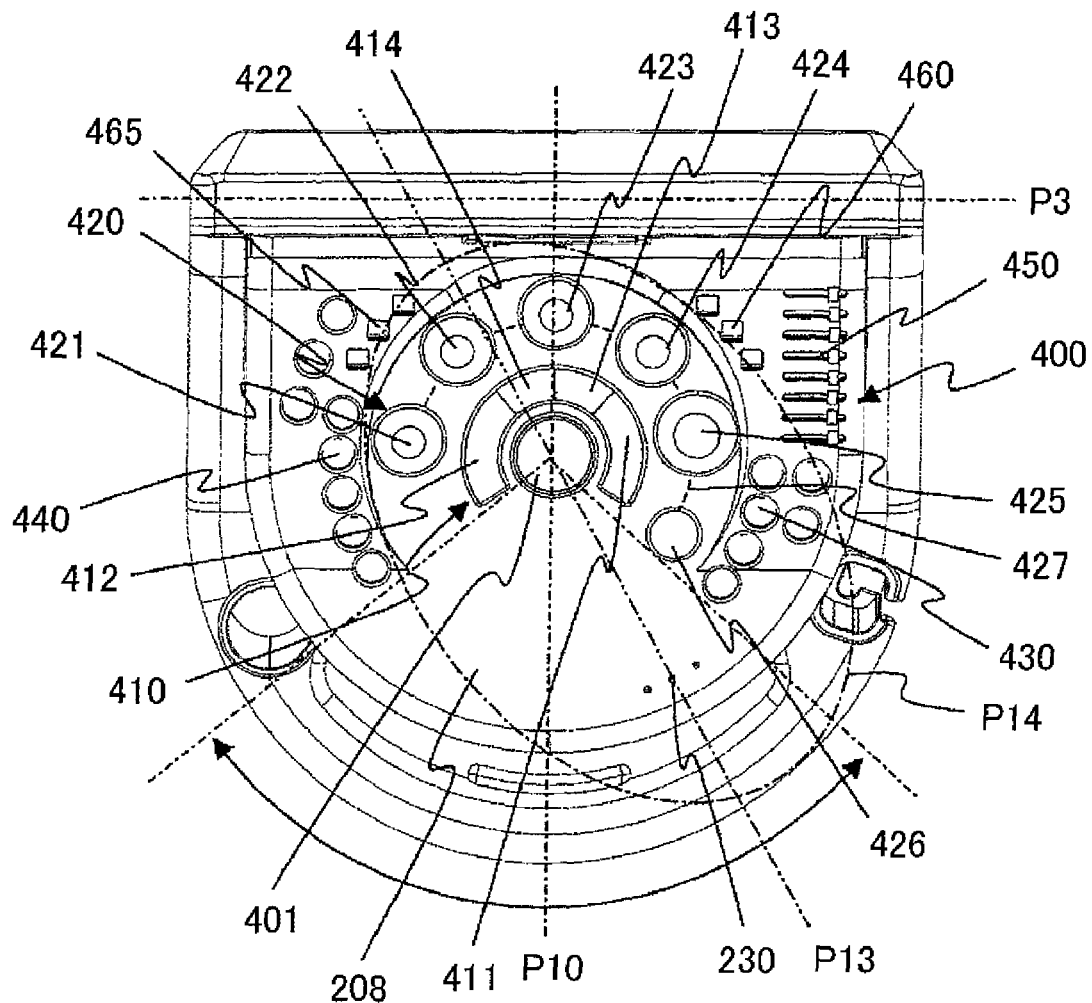
FIG. 13 shows detail views of the operation switches.
Figure 13:
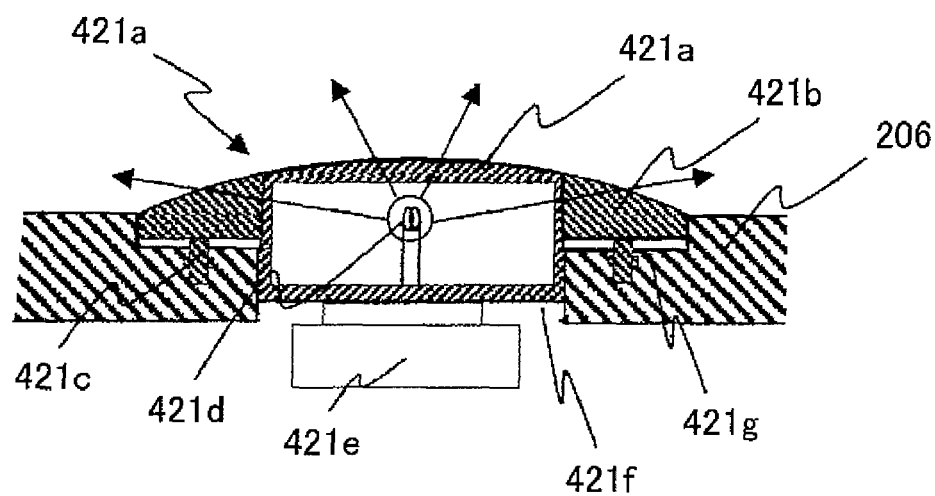
Figure 14:
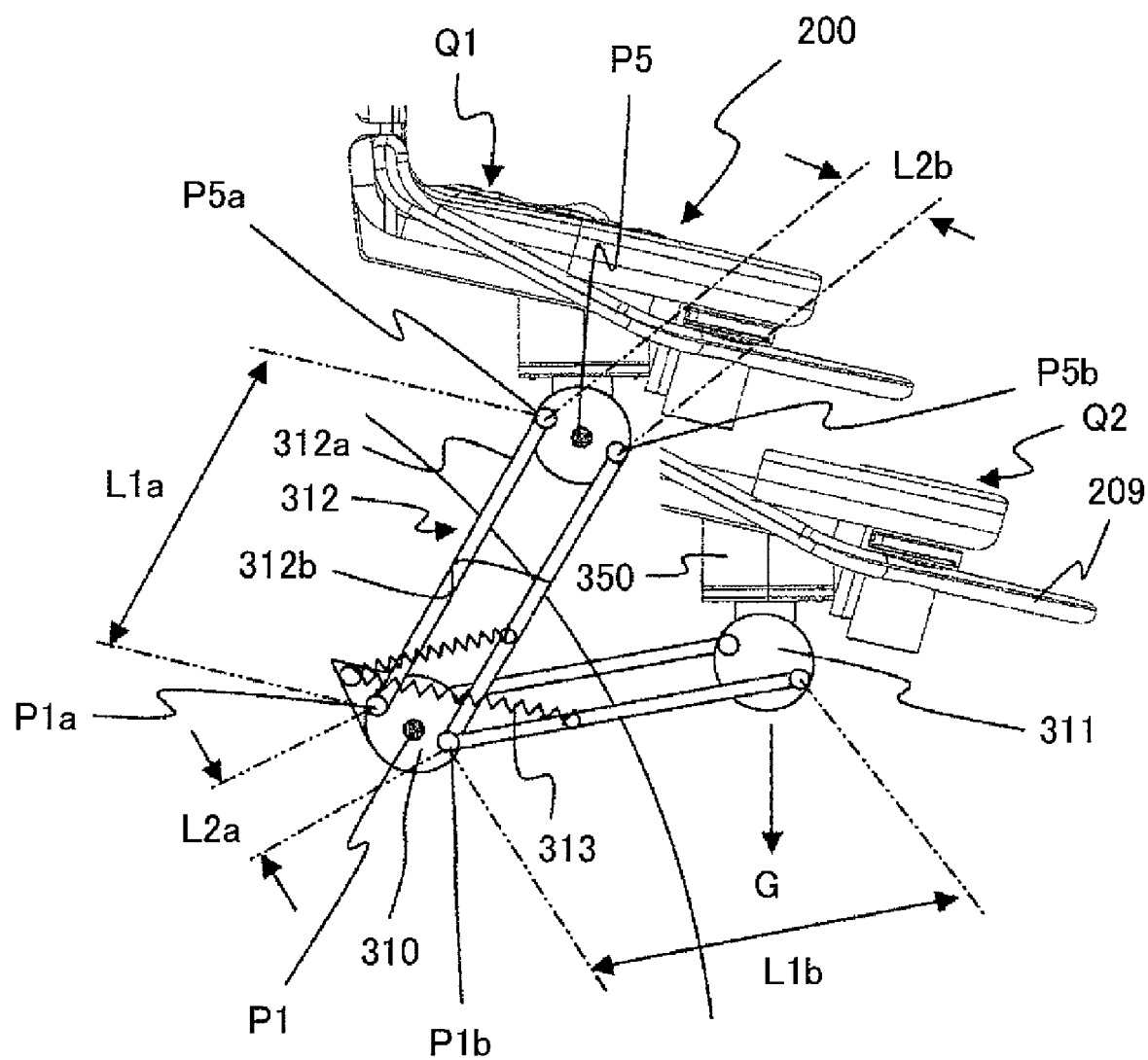
FIG. 14 is a structural view of an elevating function mechanical section.
Figure 15:
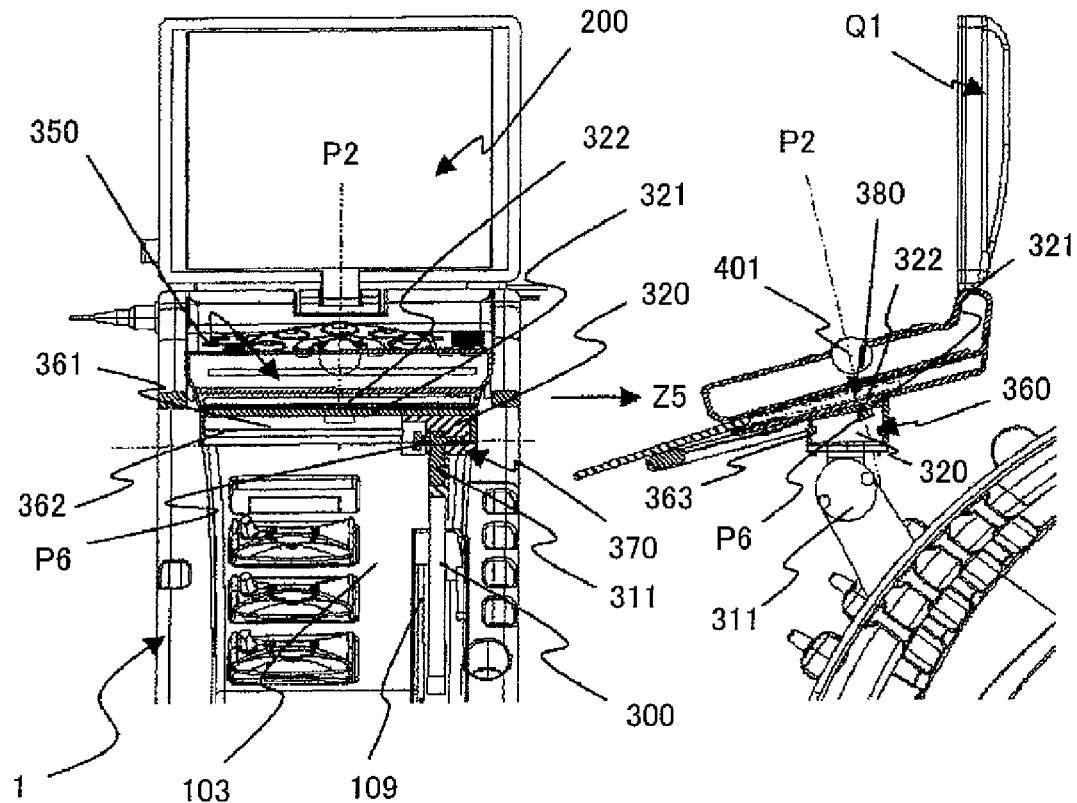
FIG. 15 shows structural views of an attachment mechanical section.
Figure 15:
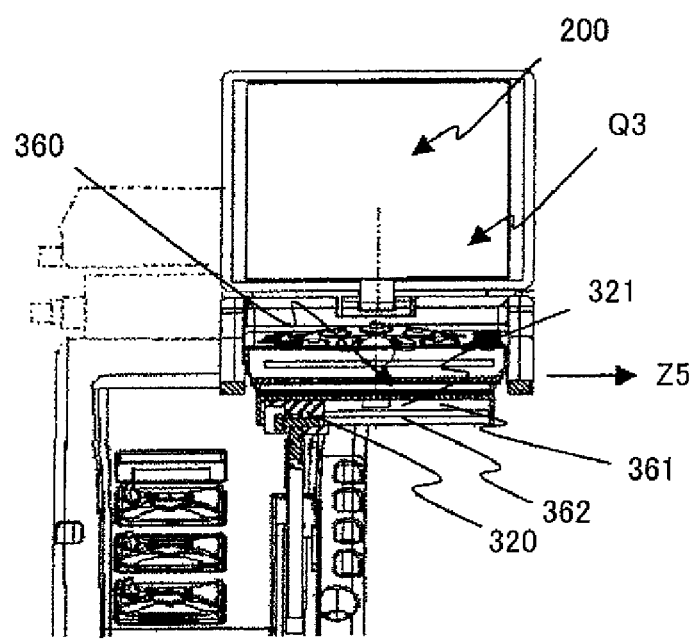
Figure 16:
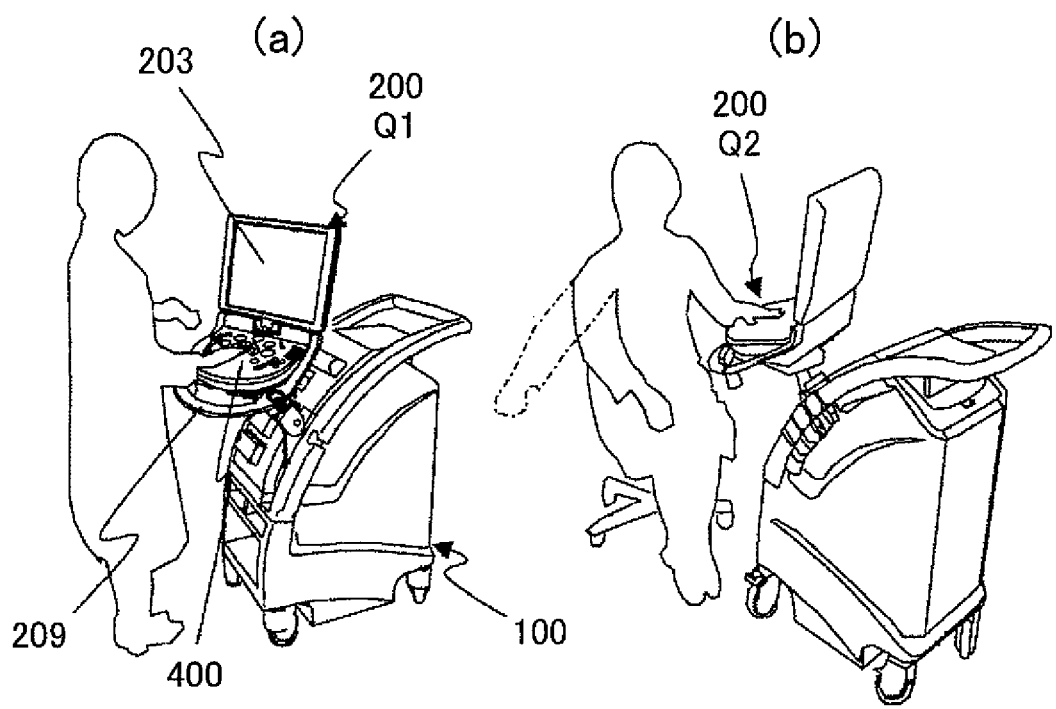
FIG. 16 shows views showing the states of operation postures when an ultrasonograph is used.
Figure 16:
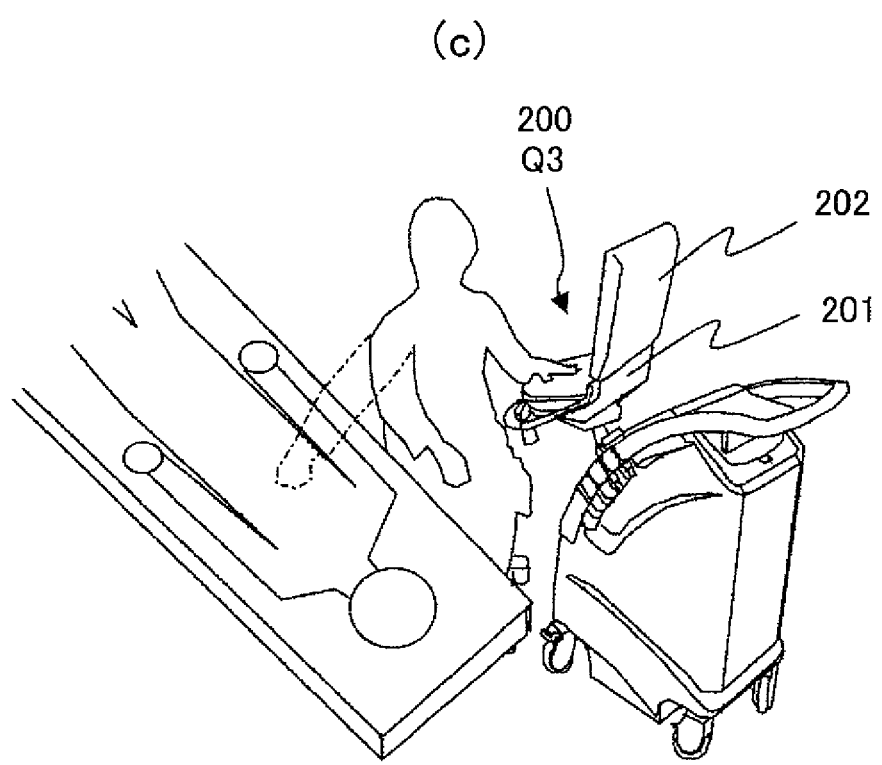
Figure 17:
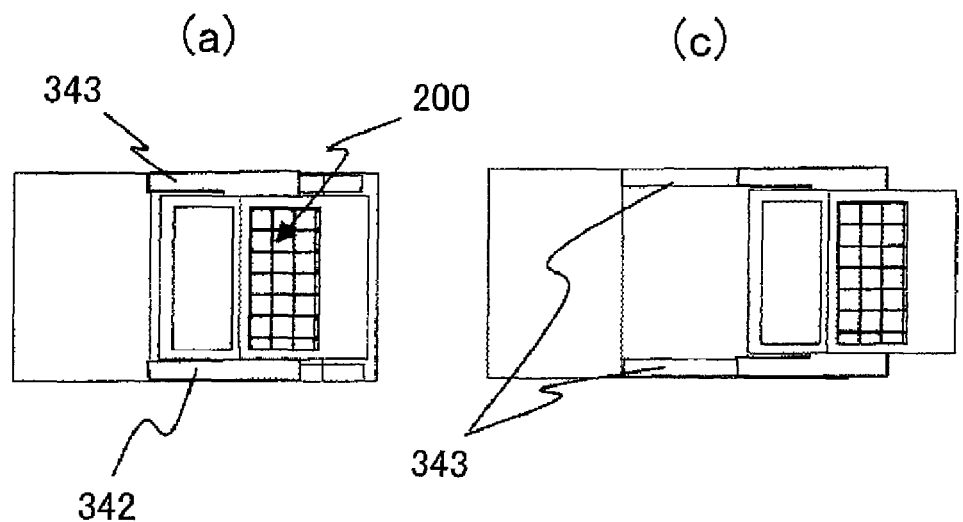
FIG. 17 shows general structural views of an elevating function mechanism container of an ultrasonograph according to the second embodiment.
Figure 17:
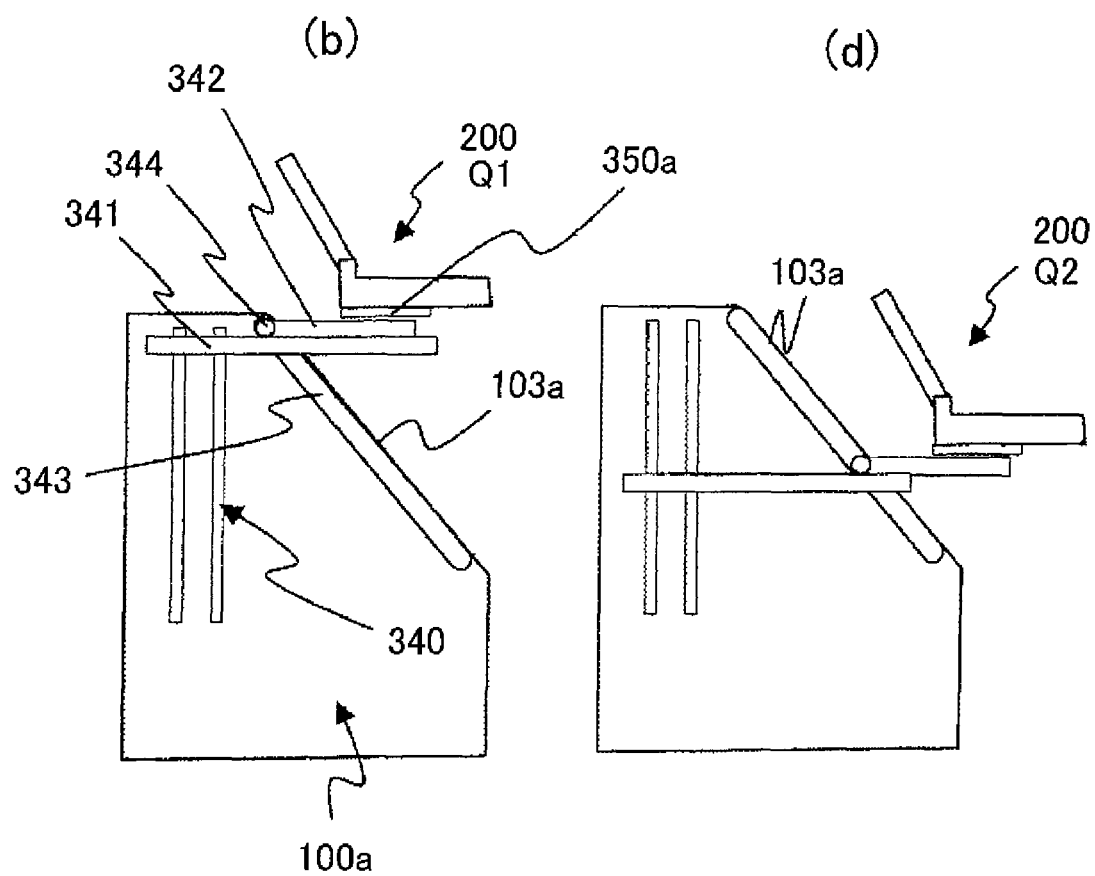

1 Ultrasonograph
1a Ultrasonograph
51 Connector device
51a Cord joint
52 Ultrasonic transceiver device
53 Control section
54 Operation device
55 DSC
56 Graphic memory
57 Monitor device
58 Ultrasonic probe
59 Auxiliary device
60 Electric power supply device
70 First device container
70a Storage rack
71 Second device container
72 Third device container
81 Video device
82 Printer
83 Jelly container
100 Main body housing
100a Main body housing
101 Universal wheel 102 Housing handle section
103 Device allocation plane
103a Device allocation plane
104 Bar-shaped grip
105 Support
106 Device allocation section
107 Table
108 Table face
109 Arm transfer groove
110 Probe container
111 Table stage
112 Device container opening
113 Container storage recess
114 Inclined plane
115 Space
116 Table container
117 Connection hinge
118 Support
200 Operation device
201 First housing
202 Second housing
203 Monitor screen
204 Operation connector
205 Bumper section
206 First housing face
207 Second housing face
208 Palm rest
209 Arched grip
210 Keyboard
211 Protrusion
212 Speaker net
213 Bumper storage space
214 Rotary support section
215 Foldable connecting shaft section
216 Intermediate joint section
217 Rotary shaft
218 Foldable connecting bearing section
219 Rotary shaft
220 Rotary bearing
221 Keyboard storage section
222 Support rail
223 Connecting pin
224 Slide groove
225 Notch
226 Recess
227 Openable lid
228 Jelly container storage section
229 Second probe container
230 Home position mark
300 Movable arm
301 Elevating function mechanical section
301a Elevating function mechanical section
302 Elevating function mechanism container
310 First base section
311 Second base section
312 Arm member
312a First arm member
312b Second arm member
313 Spring member
320 Attaching base
321 Transfer base
322 Rotation base
340 Elevator section
341 Horizontal arm
342 Slide table
343 Slide groove
344 Roller
350 Attachment mechanical section
350a Attachment mechanical section
350 Horizontal movement mechanical section
361 Recess
362 Transfer rail
363 Rail attaching section
370 Tilt mechanical section
380 Rotation mechanical section
400 Operation switches
401 Trackball
410 First circular key group
420 Second circular key group
430 Third circular key group
440 Fourth circular key group
450 Slide switch group
460 Fifth circular key group
465 Sixth circular key group
Q1 First posture
Q2 Second posture
Q3 Third posture

The invention claimed is:

1. An ultrasonograph comprising a main body to which an ultrasonic probe is connected, an operation device having an operation switch, and a movable arm connecting the main body housing and the operation device;
    wherein a bumper section is formed around and separate from the operation device; and
    wherein at least one probe container in which the ultrasonic probe is containable is formed at the bumper section in a state where the probe is enclosed by the bumper section.

2. The ultrasonograph according to claim 1,
    wherein the at least one probe container is disposed at a position which is lower than at least a position of the operation device.

3. The ultrasonograph according to claim 1,
    wherein, when the ultrasonic probe is stored in the at least one probe container, an operating area of the operation device is located at a position which is higher than a position of the stored ultrasonic probe.

4. The ultrasonograph according to claim 1,
    wherein the bumper section is located at a position which has one of a same position and a lower position than a position of a bottom face of the operation device.

5. An ultrasonograph comprising a main body housing to which an ultrasonic probe is connected, an operation device having a operation switch, and a movable arm connecting the main body housing and the operation device;
    wherein a bumper section is formed at a position which is lower than a position of the operation device so as to surround the operation device and separate from the operation device;
    wherein the operation device has a keyboard container formed at a bottom face section of the operation device, and a keyboard is slidably attached to the keyboard container;
    wherein the keyboard is formed at a position higher than the position of the bumper section;
    wherein the keyboard is slidably supported at an upper part of the bumper section; and
    wherein at least one probe container in which the ultrasonic probe is containable is formed at the bumper section in a state where the probe is enclosed by the bumper section.

6. The ultrasonograph according to claim 5,
    wherein the at least one probe container is disposed at a position which is lower than at least the position of the operation device.

7. The ultrasonograph according to claim 5,
wherein, when the ultrasonic probe is stored in the at least one probe container, an operating area of the operation device is located at a position which is higher than a position of the stored ultrasonic probe.

8. The ultrasonograph according to claim 5,
wherein the bumper section is located at a position which has one of a same position and a lower position than a position of the bottom face of the operation device.

9. An ultrasonograph comprising a main body to which an ultrasonic probe is connected, an operation device having an operation switch, and a movable arm connecting the main body housing and the operation device;
    wherein a bumper section is formed around and separate from the operation device;
    wherein a storage space of the ultrasonic probes is provided at a position inside of the bumper section; and
    wherein, when the ultrasonic probe is stored in at least one probe container in the storage space of the bumper section, the operation switch of the operation device is located at a position which is higher than a position of the stored ultrasonic probe.

* * * * *